United States Patent
Sileika et al.

(10) Patent No.: US 11,344,668 B2
(45) Date of Patent: May 31, 2022

(54) INFUSION SYSTEM WITH CONCURRENT TPN/INSULIN INFUSION

(71) Applicant: ICU Medical, Inc., San Clemente, CA (US)

(72) Inventors: Tadas S. Sileika, Vernon Hills, IL (US); Justin J. Schmidt, Grayslake, IL (US); William Kenneth Day, Hoffman Estates, IL (US); James B. Brown, Lake Forest, IL (US)

(73) Assignee: ICU Medical, Inc., San Clemente, CA (US)

( * ) Notice: Subject to any disclaimer, the term of this patent is extended or adjusted under 35 U.S.C. 154(b) by 475 days.

(21) Appl. No.: 14/972,585

(22) Filed: Dec. 17, 2015

(65) Prior Publication Data

US 2016/0175517 A1    Jun. 23, 2016

Related U.S. Application Data

(60) Provisional application No. 62/094,552, filed on Dec. 19, 2014.

(51) Int. Cl.
*A61M 5/14* (2006.01)
*A61M 5/145* (2006.01)
(Continued)

(52) U.S. Cl.
CPC .......... *A61M 5/1408* (2013.01); *A61K 9/0029* (2013.01); *A61K 38/28* (2013.01);
(Continued)

(58) Field of Classification Search
CPC ............ A61M 5/1408; A61M 5/16827; A61M 5/1452; A61M 5/1723; A61M 2205/18;
(Continued)

(56) References Cited

U.S. PATENT DOCUMENTS 3,401,337 A    9/1968   Beusman et al.
3,484,681 A    12/1969  Grady, Jr. et al.
(Continued)

FOREIGN PATENT DOCUMENTS

AU    2013216679    9/2013
BR    PI0704229-9   11/2009
(Continued)

OTHER PUBLICATIONS

ALARIS® Medical Systems, "Signature Edition® GOLD—Single & Dual Channel Infusion System", San Diego, CA, USA, date unknown, but believed to be at least as early as Nov. 29, 2008, pp. 70-74, 2-88 & 2-91.

(Continued)

*Primary Examiner* — Lauren P Farrar
*Assistant Examiner* — Hamza A Darb
(74) *Attorney, Agent, or Firm* — Knobbe Martens Olson & Bear, LLP

(57) ABSTRACT

An infusion system to provide concurrent TPN/insulin infusion including: a fluid administration set having a primary line in fluid communication with the TPN source, a secondary line in fluid communication with the insulin source, and a common outlet line; a pump operable to removably receive the fluid administration set, the pump being operable to concurrently move the TPN solution through the primary line in response to a TPN solution flow rate signal and the insulin solution through the secondary line in response to an insulin solution flow rate signal; and a flow controller operable to provide the TPN solution flow rate signal and the insulin solution flow rate signal to the pump. The flow controller is further operable to vary the TPN solution flow rate signal and the insulin solution flow rate signal to vary a ratio of TPN solution to insulin solution provided to the common outlet line.

17 Claims, 20 Drawing Sheets

(51) Int. Cl.
*A61M 5/168* (2006.01)
*A61M 5/172* (2006.01)
*A61K 9/00* (2006.01)
*A61K 38/28* (2006.01)

(52) U.S. Cl.
CPC ...... *A61M 5/1452* (2013.01); *A61M 5/16827* (2013.01); *A61M 5/1723* (2013.01); *A61M 2205/18* (2013.01); *A61M 2205/3334* (2013.01); *A61M 2205/502* (2013.01); *A61M 2230/005* (2013.01); *A61M 2230/201* (2013.01)

(58) Field of Classification Search
CPC ...... A61M 2205/502; A61M 2230/201; A61M 2205/3334; A61M 2230/005; A61M 2005/14208; A61M 5/168; A61K 9/0029; A61K 38/28
See application file for complete search history.

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |

(56) References Cited

U.S. PATENT DOCUMENTS

| | | |
|---|---|---|
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalaute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | Kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Bloomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Laenen et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |

(56) References Cited

U.S. PATENT DOCUMENTS

| | | |
|---|---|---|
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | After |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |

(56) References Cited

U.S. PATENT DOCUMENTS

| | | |
|---|---|---|
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillen et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |

(56) References Cited

U.S. PATENT DOCUMENTS

| | | |
|---|---|---|
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |

(56) References Cited

U.S. PATENT DOCUMENTS

| | | |
|---|---|---|
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,875,195 B2 | 4/2005 | Choi |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouola et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Gimdt |
| 7,294,109 B2 | 11/2007 | Lovett et al. |
| 7,296,482 B2 | 11/2007 | Schaffer et al. |
| 7,300,418 B2 | 11/2007 | Zaleski |

(56) References Cited

U.S. PATENT DOCUMENTS

| | | | |
|---|---|---|---|
| 7,305,883 B2 | 12/2007 | Khuri-Yakub et al. |
| 7,327,273 B2 | 2/2008 | Hung et al. |
| 7,338,470 B2 | 3/2008 | Katz |
| 7,347,836 B2 | 3/2008 | Peterson et al. |
| 7,347,854 B2 | 3/2008 | Shelton et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenkow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,981,073 B2 | 7/2011 | Mollstam |
| 7,981,082 B2 | 7/2011 | Wang et al. |
| 8,002,736 B2 | 8/2011 | Patrick et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blomquist |
| 8,175,668 B1 | 5/2012 | Nabutovsky et al. |
| 8,177,739 B2 | 5/2012 | Cartledge et al. |
| 8,185,322 B2 | 5/2012 | Schroeder et al. |
| 8,219,413 B2 | 7/2012 | Martinez et al. |
| 8,221,395 B2 | 7/2012 | Shelton et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,449,524 B2 | 5/2013 | Braig et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| 9,190,010 B2 | 11/2015 | Vik et al. |
| 9,240,002 B2 | 1/2016 | Hume et al. |
| 9,272,089 B2 | 3/2016 | Jacobson et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,707,341 B2 | 7/2017 | Dumas, III et al. |
| 9,764,087 B2 | 9/2017 | Peterfreund et al. |
| 9,852,265 B1 | 12/2017 | Treacy et al. |
| 9,943,269 B2 | 4/2018 | Muhsin et al. |
| 9,995,611 B2 | 6/2018 | Ruchti et al. |
| 10,022,498 B2 | 7/2018 | Ruchti et al. |
| 10,046,112 B2 | 8/2018 | Oruklu et al. |
| 10,089,055 B1 | 10/2018 | Fryman |
| 10,166,328 B2 | 1/2019 | Oruklu et al. |
| 10,342,917 B2 | 7/2019 | Shubinsky et al. |
| 10,430,761 B2 | 10/2019 | Hume et al. |
| 10,463,788 B2 | 11/2019 | Day |
| 2001/0007636 A1 | 7/2001 | Butterfield |

(56) References Cited

U.S. PATENT DOCUMENTS

| | | |
|---|---|---|
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0168278 A1 | 11/2002 | Jeon et al. |
| 2002/0173703 A1 | 11/2002 | Lebel et al. |
| 2002/0183693 A1* | 12/2002 | Peterson ............ A61M 5/14228 604/151 |
| 2003/0009244 A1 | 1/2003 | Engleson |
| 2003/0013959 A1 | 1/2003 | Grunwald et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0141981 A1 | 7/2003 | Bui |
| 2003/0143746 A1 | 7/2003 | Sage, Jr. |
| 2003/0144878 A1 | 7/2003 | Wilkes et al. |
| 2003/0158508 A1* | 8/2003 | DiGianfilippo ..... G06F 19/3456 604/4.01 |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0186833 A1 | 10/2003 | Huff et al. |
| 2003/0187338 A1 | 10/2003 | Say et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0216682 A1 | 11/2003 | Junker |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0145114 A1 | 6/2004 | Ippolito et al. |
| 2004/0128162 A1 | 7/2004 | Schlotterbeck et al. |
| 2004/0133166 A1 | 7/2004 | Moberg et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0247445 A1 | 12/2004 | Nelson |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1* | 1/2005 | Campbell .......... A61B 5/14532 604/131 |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0204828 A1 | 9/2005 | Lee et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |

(56) References Cited

U.S. PATENT DOCUMENTS

| | | |
|---|---|---|
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1* | 1/2006 | O'Mahony ........ A61B 5/14532 604/4.01 |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1* | 4/2006 | Small ................ A61M 5/14546 600/432 |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1* | 5/2006 | Eggers ................ A61B 5/417 705/3 |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1* | 6/2006 | Eggers ................ G16H 40/40 705/2 |
| 2006/0135939 A1 | 6/2006 | Brown |
| 2006/0135940 A1 | 6/2006 | Joshi |
| 2006/0136271 A1* | 6/2006 | Eggers ................ G16H 40/40 705/3 |
| 2006/0140798 A1 | 6/2006 | Kutsuzawa |
| 2006/0143051 A1* | 6/2006 | Eggers ................ G16H 40/40 705/3 |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1* | 8/2006 | Eggers ................ G16H 40/40 705/3 |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229557 A1 | 10/2006 | Fathallah et al. |
| 2006/0229918 A1 | 10/2006 | Fotsch et al. |
| 2006/0235353 A1 | 10/2006 | Gelfand et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0265246 A1 | 11/2006 | Hoag |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1* | 4/2007 | Williams, Jr. ........ A61M 5/172 604/65 |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0179436 A1 | 8/2007 | Braig et al. |
| 2007/0191817 A1 | 8/2007 | Martin |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1* | 3/2008 | Moubayed ............ A61M 5/172 604/67 |
| 2008/0071496 A1 | 3/2008 | Glascock |
| 2008/0071580 A1 | 3/2008 | Marcus et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0200870 A1 | 8/2008 | Palmroos et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0243055 A1 | 10/2008 | Fathallah et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0112155 A1 | 4/2009 | Zhao |
| 2009/0114037 A1 | 5/2009 | Smith |
| 2009/0124963 A1 | 5/2009 | Hogard et al. |
| 2009/0124964 A1 | 5/2009 | Leach et al. |
| 2009/0131861 A1* | 5/2009 | Braig ................ A61B 5/1427 604/66 |
| 2009/0135196 A1 | 5/2009 | Holland et al. |

(56) References Cited

U.S. PATENT DOCUMENTS

| | | |
|---|---|---|
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1* | 7/2010 | Robinson ............ A61B 5/14532 600/309 |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0214110 A1 | 8/2010 | Wang et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0317093 A1 | 12/2010 | Turewicz et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1* | 2/2011 | Eggers ................ A61M 5/1413 604/19 |
| 2011/0040247 A1 | 2/2011 | Mandro et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0137241 A1 | 6/2011 | DelCastilio et al. |
| 2011/0144595 A1 | 6/2011 | Cheng |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0320049 A1 | 12/2011 | Chossat et al. |
| 2012/0025995 A1 | 2/2012 | Moberg et al. |
| 2012/0035535 A1 | 2/2012 | Johnson et al. |
| 2012/0059234 A1 | 3/2012 | Barrett et al. |
| 2012/0068001 A1 | 3/2012 | Pushkarsky et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0041342 A1 | 2/2013 | Bernini et al. |
| 2013/0083191 A1 | 4/2013 | Lowery et al. |
| 2013/0085443 A1 | 4/2013 | Lowery et al. |
| 2013/0085689 A1 | 4/2013 | Sur et al. |
| 2013/0110538 A1 | 5/2013 | Butterfield et al. |
| 2013/0150766 A1 | 6/2013 | Oide et al. |
| 2013/0150821 A1 | 6/2013 | Bollish et al. |
| 2013/0158504 A1 | 6/2013 | Ruchti et al. |
| 2013/0197930 A1 | 8/2013 | Garibaldi et al. |
| 2013/0201482 A1 | 8/2013 | Munro |
| 2013/0116649 A1 | 9/2013 | Kouyoumjian et al. |
| 2013/0253430 A1 | 9/2013 | Kouyoumjian et al. |
| 2013/0261993 A1 | 10/2013 | Ruchti et al. |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0345658 A1 | 12/2013 | Browne et al. |
| 2013/0345666 A1 | 12/2013 | Panduro et al. |
| 2014/0039446 A1 | 2/2014 | Day |
| 2014/0224829 A1 | 8/2014 | Capone et al. |
| 2014/0267563 A1 | 9/2014 | Baca et al. |
| 2014/0350513 A1 | 11/2014 | Oruklu et al. |
| 2014/0358077 A1 | 12/2014 | Oruklu et al. |
| 2015/0025453 A1 | 1/2015 | Ledford et al. |
| 2015/0033073 A1 | 1/2015 | Yang et al. |
| 2015/0168958 A1* | 6/2015 | Downie ............... G05D 11/137 700/282 |
| 2015/0224252 A1 | 8/2015 | Borges et al. |
| 2015/0246175 A1 | 9/2015 | Shubinsky et al. |
| 2015/0343141 A1 | 12/2015 | Lindo et al. |
| 2016/0042264 A1 | 2/2016 | Borges et al. |
| 2016/0103960 A1 | 4/2016 | Hume et al. |
| 2016/0110088 A1 | 4/2016 | Vik et al. |
| 2016/0151560 A1* | 6/2016 | Toro ..................... A61M 5/142 604/151 |
| 2016/0151562 A1* | 6/2016 | Magers ................ A61M 5/142 604/500 |

(56) References Cited

U.S. PATENT DOCUMENTS

| | | | |
|---|---|---|---|
| 2016/0151601 | A1 | 6/2016 | Cardelius et al. |
| 2016/0193604 | A1 | 7/2016 | McFarland et al. |
| 2016/0256622 | A1 | 9/2016 | Day et al. |
| 2016/0339167 | A1 | 11/2016 | Ledford et al. |
| 2017/0043089 | A1 | 2/2017 | Handler |
| 2018/0018440 | A1 | 1/2018 | Sugawara |
| 2018/0028749 | A1 | 2/2018 | Dumas, III et al. |
| 2019/0091401 | A1 | 3/2019 | Ruchti et al. |
| 2019/0101425 | A1 | 4/2019 | Ruchti et al. |
| 2019/0117890 | A1 | 4/2019 | Oruklu et al. |
| 2019/0196770 | A1 | 6/2019 | Fryman |
| 2019/0262535 | A1 | 8/2019 | Shubinsky et al. |
| 2019/0282757 | A1 | 9/2019 | Gylland et al. |

FOREIGN PATENT DOCUMENTS

| | | |
|---|---|---|
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 519 765 | 12/1992 |
| EP | 0516 130 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813188 | 8/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2717919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-520270 | 7/2007 |
| JP | 2008-249400 | 10/2008 |
| JP | 4322661 | 6/2009 |
| JP | 2010-063767 | 3/2010 |
| NZ | 614053 | 9/2015 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 98/057064 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 01/033710 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/070556 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |

(56) References Cited

FOREIGN PATENT DOCUMENTS

| WO | WO 2009/016504 | 2/2009 |
|---|---|---|
| WO | WO 2009/023406 | 2/2009 |
| WO | WO 2009/023407 | 2/2009 |
| WO | WO 2009/023634 | 2/2009 |
| WO | WO 2009/026420 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | 2010/135670 A2 | 11/2010 |
| WO | WO 2010/135646 | 11/2010 |
| WO | WO 2010/135654 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/167090 | 12/2012 |
| WO | WO 2013/028524 | 2/2013 |
| WO | 2013/096769 A1 | 6/2013 |
| WO | WO 2015/134478 | 9/2015 |
| WO | WO 2017/051271 | 3/2017 |
| WO | WO 2017/197024 | 11/2017 |
| WO | WO 2017/214441 | 12/2017 |

OTHER PUBLICATIONS

Buhrdorf et al., "Capacitive Micromachined Ultrasonic Transducers and their Application", Proceedings of the IEEE Ultrasonics Symposium, Feb. 2001, vol. 2, pp. 933-940.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http//www.diffen.com/difference/Continually vs Continuously, as accessed Aug. 13, 2009 in 4 pages.
"CritiCore® Monitor: Critical Fluid Output and Core Bladder Temperautre Monitor", BARD Urological Catheter Systems, Advertisement, 2005, pp. 2.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
"Froth", http://www.merriam-webster.com/dictionary/froth, as accessed May 13, 2015 in 1 page.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
JMS Co., Ltd., "Infusion Pump: OT-701", Tokyo, Japan, 2002, pp. 4.
Kutcher et al., "The Effect of Lighting Conditions on Caries Interpretation with a Laptop Computer in a Clinical Setting", Elsevier, Oct. 2006, vol. 102, No. 4, pp. 537-543.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Merry et al., "A New, Safety-Oriented, Integrated Drug Administration and Automated Anesthesia Record System", Anesthesia & Analgesia, Aug. 2001, vol. 93, No. 2 pp. 385-390.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-releases/2014/05 08 14 sigma.page.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Diabetes Close up, Close Concerns AACE Inpatient Management Conference Report, Consensus Development Conference on Inpatient Diabetes and Metabolic Control, Washington, D.C., Dec. 14-16, 2003, pp. 1-32.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. www.hospira.com/products and services/infusion pumps/plum/index.
Hospira, "Plum XL™ Series Infusion System" Technical Service Manual, Feb. 2005, Lake Forest, Illinois, USA, pp. i-vii, 5-14, 8-3.
International Preliminary Report on Patentability and Written Opinion received in PCT Application No. PCT/US2015/066595, dated Jun. 29, 2017 in 10 pages.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Microchip Technology Inc., "MTA11200B; TrueGauge™ Intelligent Battery Management I.C.", https://www.elektronik.ropla.eu/pdf/stock/mcp/mta11200b.pdf, 1995, pp. 44.
Moghissi, Etie, MD, FACP, FACE, "Hyperglycemia in Hospitalized Patients", A Supplement to AGP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.

(56) References Cited

OTHER PUBLICATIONS

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.
Van Den Berghe, M.D., Ph.D., et al., "Intensive Insulin Therapy in Critically III Patients", The New England Journal of Medicine, Novembers, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely III Patients", Critical Care Medicine, 2008, vol. 36, No. 5, pp. 1507-1512.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. http://archive.epo.org/epo/pubs/oj013/11 13/11 5033.pdf.
"Decision of the Administrative Council of Oct. 27, 2009 Amending the Implementing Regulations to the European Patent Convention (CA/D 20/09)", Official Journal EPO Dec. 2009, Dec. 2009, pp. 582-584. http://archive.epo.org/epo/pubs/0j009/12 09/12 5829.pdf.
Alaedeen et al., "Total parenteral nutrition-associated hyperglycemia correlates with prolonged mechanical ventilation and hospital stay in septic infants", Journal of Pediatric Surgery 41:239-244 (2006).
Beers et al. The Merck Manual of Medical Information (Merck Research Laboratories, 2003).
Binder et al., "Insulin infusion with parenteral nutrition in extremely low birth weight infants with hyperglycemia", The Journal of Pediatrics 114(2):273-280 (1989).
Bode et al., "Intravenous Insulin Infusion Therapy: Indications, Methods, and Transition to Subcutaneous Insulin Therapy", Endocrine Practice 10(Suppl 2):71-80 (2004).
Cheung et al., "Hyperglycemia is Associated With Adverse Outcomes in Patients Receiving Total Parenteral Nutrition", Diabetes Care 28(10):2367-2371 (2005).
International Application No. PCT/US2015/66595, International Search Report and Written Opinion, dated Feb. 25, 2016.
Magaji et al., "Inpatient Management of Hyperglycemia and Diabetes", Clinical Diabetes 29(1):3-9 (2011).
Maynard et al., "Subcutaneous Insulin Order Sets and Protocols: Effective Design and Implementation Strategies", Journal of Hospital Medicine 3(S5):29-41 (2008).
Thomas et al., "Implementation of a tight glycaemic control protocol using a web-based insulin dose calculator", Anaesthesia 60:1093-1100 (2005).

\* cited by examiner

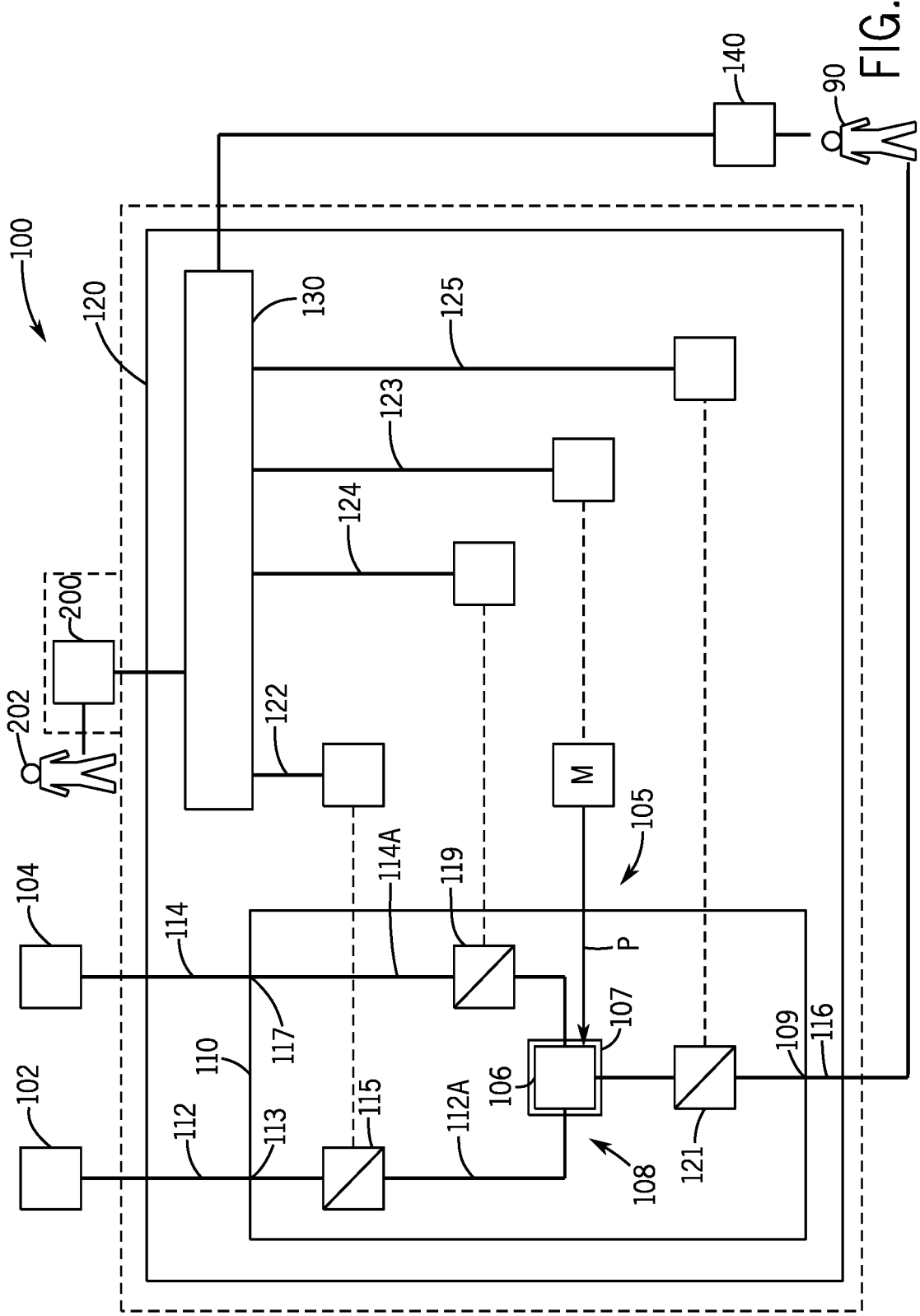

INFUSION SYSTEM WITH CONCURRENT TPN/INSULIN INFUSION

TECHNICAL FIELD

The present invention relates to medical devices. More specifically, the invention relates to infusion systems with concurrent total parenteral nutrition (TPN)/insulin infusion.

BACKGROUND OF THE INVENTION

Infusion pumps are medical devices that deliver fluids, including nutrients and medications such as antibiotics, chemotherapy drugs, and pain relievers, into a patient's body in controlled amounts. Many types of pumps, including large volume, patient-controlled analgesia (PCA), elastomeric, syringe, enteral, and insulin pumps, are used worldwide in healthcare facilities such as hospitals, and in the home. Clinicians and patients rely on pumps for safe and accurate administration of fluids and medications.

Total parenteral nutrition (TPN) is used to feed a person intravenously when the gastrointestinal tract is nonfunctional or impaired, so that nutrition cannot be provided to the patient through eating. TPN solution can include sugar, carbohydrates, proteins, lipids, electrolytes, trace elements, and various combinations thereof, as required for a particular patient.

Unfortunately, hyperglycemia is one complication associated with administration of TPN. Recent studies have highlighted that hyperglycemia is associated with increased risk of cardiac complications, infection, systemic sepsis, acute renal failure, and death for patients receiving TPN. Glycemic control in these patients is crucial in maintenance of tolerable blood glucose levels, a fact further substantiated by correlated adverse outcomes.

In present practice, TPN solution administration is tapered to 50% of the required dosing for the patient to minimize hyperglycemia and avoid glucose shock. Insulin is premixed in the same IV bag or container with the TPN solution based on calculated requirements for the patient, adding to clinician time and risk of error. Insulin dosing also requires modulation based on monitored glucose levels during infusion. Subcutaneous insulin infusions can be administered to compensate for advancing hyperglycemia. For hypoglycemic situations, increased TPN (and specifically dextrose) delivery is indicated. Thus, infusion of both TPN and insulin as presently practiced is complex and time consuming.

It would be desirable to have an infusion system with concurrent TPN/insulin infusion that would overcome the above disadvantages.

SUMMARY OF THE INVENTION

One aspect of the present invention provides an infusion system for a patient for use with a TPN source of TPN solution and separate insulin source of insulin solution to provide concurrent TPN/insulin infusion, the infusion system including: a fluid administration set having a primary line in fluid communication with the TPN source, a secondary line in fluid communication with the insulin source, and a common outlet line in fluid communication with the primary line, the secondary line, and the patient; a pump operable to removably receive the fluid administration set, the pump being operable to concurrently move the TPN solution through the primary line in response to a TPN solution flow rate signal and the insulin solution through the secondary line in response to an insulin solution flow rate signal; and a flow controller operable to provide the TPN solution flow rate signal and the insulin solution flow rate signal to the pump. The flow controller is further operable to vary the TPN solution flow rate signal and the insulin solution flow rate signal to vary a ratio of TPN solution to insulin solution provided to the patient from the common outlet line.

Another aspect of the present invention provides a method to concurrently deliver a TPN solution from a TPN source and an insulin solution from separate insulin source, the method including: providing a fluid administration set having a primary line, a secondary line, a common outlet line, and a pumping/mixing chamber between and in fluid communication with the primary line, the secondary line, and common outlet line; connecting the primary line to the TPN source; connecting the secondary line to the insulin source; allowing TPN fluid into the pumping/mixing chamber; allowing insulin solution into the pumping/mixing chamber; mixing the TPN solution and the insulin solution to generate an infusion mixture before the common outlet; with a positive displacement pump, driving the TPN solution through the common outlet line at a TPN dose rate and with a positive displacement pump, driving the insulin solution through the common outlet line at an insulin dose rate; and varying at least one of the TPN dose rate and the insulin dose rate to vary a ratio of TPN solution to insulin solution in the infusion mixture.

The foregoing and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 1A is a block diagram of an infusion system with concurrent TPN/insulin infusion in accordance with one embodiment of the present invention;

Like elements share like reference numbers throughout the various figures.

DETAILED DESCRIPTION OF PRESENTLY PREFERRED EMBODIMENTS

Figure 1:
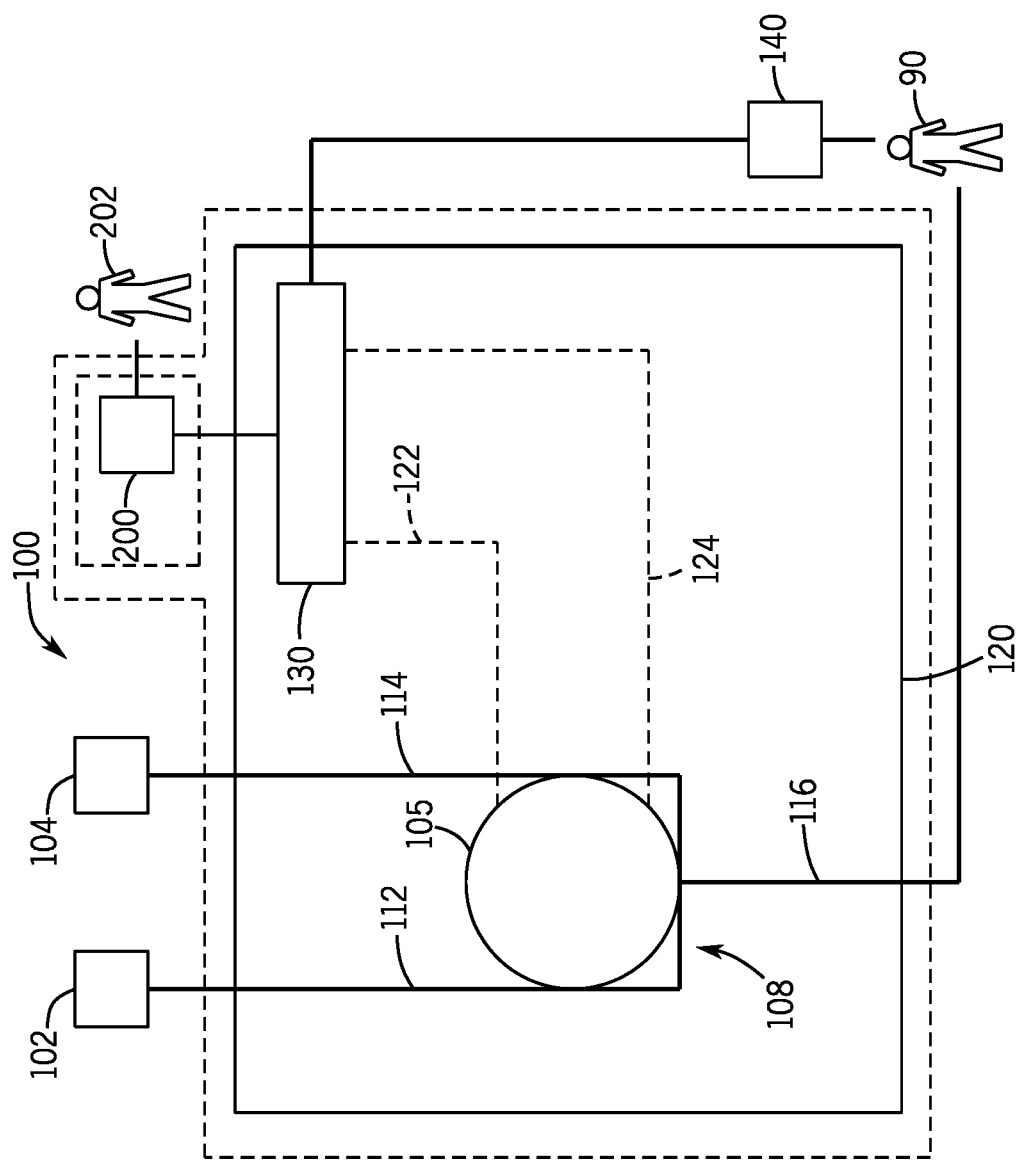
FIG. 1 is a block diagram of an infusion system with concurrent TPN/insulin infusion in accordance with the present invention.

FIG. 1 is a block diagram of an infusion system with concurrent TPN/insulin infusion in accordance with the present invention. The infusion system 100 for a patient 90 is for use with a TPN source or source container 102 of TPN solution and a separate insulin source or source container 104 of insulin solution. The infusion system 100 can concurrently deliver the TPN solution and the insulin solution, without requiring that the insulin be premixed in the same IV bag or container as the TPN solution or be administered by syringe boluses subcutaneously or a different pump or flow controller.

The infusion system 100 includes a fluid administration set 108, a pump 120 operable to removably receive the administration set 108, and a flow controller 130 operable to control flow through the administration set 108. The administration set 108 has a primary line 112 in fluid communication with the TPN source 102, a secondary line 114 in fluid communication with the insulin source 104, and a common outlet line 116 connected to and in operative fluid communication with the primary line 112, the secondary line 114, and the patient 90. The infusion system 100 can optionally include a glucose sensor 140 for providing feedback to the flow controller 130 and/or a user interface 200 providing input and/or output to a user 202. The user interface 200 can be integral to or can be separate from the infusion system 100. In one example, the user interface 200 is wired into the infusion system 100. In another example, the user interface 200 communicates wirelessly with the infusion system 100. The user 202 can be the patient 90 themselves or a caregiver of the patient 90.

In one embodiment, the pump 120 is a positive displacement pump and has a drive mechanism 105 that is operable on the fluid administration set 108 to concurrently move the TPN solution through the primary line 112 to the outlet line 116 in response to a TPN solution flow rate signal 122 and the insulin solution through the secondary line 114 to the outlet line 116 in response to an insulin solution flow rate signal 124. The flow controller 130 is operable to provide the TPN solution flow rate signal 122 and the insulin solution flow rate signal 124 to the drive mechanism 105 of the pump. The flow controller 130 is further operable to vary the TPN solution flow rate signal 122 and the insulin solution flow rate signal 124 to vary a ratio of TPN solution to insulin solution provided to the common outlet line 116.

As best seen in FIG. 1A, in one embodiment the fluid administration set 108 comprises a cassette 110 including a primary inlet 113 joining a primary fluid passageway 112A in the cassette 110 into fluid communication with the primary line 112, a secondary inlet 117 joining a secondary fluid passageway 114A in the cassette into fluid communication with the secondary line 114, an outlet 109 in fluid communication with the outlet line 116, and a pumping/mixing chamber 106 covered by a resilient flexible membrane 107 and in fluid communication with the primary fluid passageway 112A, the secondary fluid passageway 114A, and the outlet 109. The drive mechanism 105 includes a motor M driving a plunger P into the membrane 107 covering the pumping/mixing chamber 106 in a reciprocating manner in response to a motor drive signal 123 from the flow controller 130. In addition, the flow controller 130 provides control signals 122, 124 and 125 respectively to operate a primary inlet valve 115, a secondary inlet valve 119 and an outlet valve 121 so as to mix and displace fluid from the pumping/mixing chamber 106 through the outlet 109 into the outlet line 116 with each cycle of the plunger P. In one embodiment, the motor M is a stepper motor that extends and retracts the plunger P to displace fluid from the pumping/mixing chamber 106. Therefore, the pump 120 acts on the cassette 110 and is operable to concurrently move the TPN solution through the primary line 112 in response to a TPN solution flow rate signal 122 and the insulin solution through the secondary line 114 in response to an insulin solution flow rate signal 124. The flow controller 130 is operable to provide to the pump 120 the TPN solution flow rate signal 122 and the insulin solution flow rate signal 124. The flow controller 130 is further operable to vary the TPN solution flow rate signal 122 and the insulin solution flow rate signal 124 to vary a ratio of TPN solution to insulin solution provided from the common outlet 116 to the patient 90. Thus, the flow controller 130 can vary the ratio of TPN solution to insulin solution in the infusion solution with time, as desired for a particular application. In one embodiment, the pump 120 is a Plum A+™ general purpose infusion system available from Hospira, Inc. of Lake Forest, Ill. The cassette 110 is also available from Hospira, Inc. under the trademark PLUMSET™.

The TPN source 102 of TPN solution and the insulin source 104 of insulin solution can be any containers operable to hold liquid, such as an intravenous (IV) bag, rigid IV container, a syringe, or the like. The TPN solution can be any solution for total parenteral nutrition (TPN) and can include sugar, carbohydrates, proteins, lipids, electrolytes, trace elements, and the like, as required for a particular application. The insulin solution can include insulin in a solution such as in a saline solution, TPN solution, or the like. The concentration of the TPN solution and the insulin solution remain constant during the concurrent TPN/insulin infusion.

The pump 120 can be any pump operable to receive a fluid administration set in general or a cassette in particular. In one example, the cassette is a disposable cassette. In one example, the pump 120 pressurizes the primary line 112 and the secondary line 114, and valves in each of the primary line 112 and the secondary line 114 of the disposable cassette 110 govern the flow rate in each of the primary line 112 and the secondary line 114. In another example, the pump 120 varies impeller speed for impellers in each of the primary line 112 and the secondary line 114 to govern the flow rate in each of the primary line 112 and the secondary line 114.

Those skilled in the art will appreciate that the flow controller 130 can include a processor and a memory coupled to the processor. The memory can contain programming code executable by the processor to carry out a method of concurrent TPN/insulin infusion as described herein.

The flow controller 130 can provide a TPN ramp phase, a TPN continuous phase, a TPN taper phase, and/or a TPN Keep Vein Open (KVO) phase during the concurrent TPN/insulin infusion as desired for a particular application. One skilled in the art will recognize in view of the present disclosure that the TPN KVO phase is really just a special case of a Continue at the Same or Different Rate TPN phase.

The TPN ramp phase ramps the TPN flow rate through the primary line 112 from zero to the TPN flow rate for the TPN continuous phase, such as can be used at the beginning of the concurrent TPN/insulin infusion. An exemplary TPN ramp phase is illustrated at Ramp portion 610 of FIG. 6. Referring to FIG. 1, for the TPN ramp phase the flow controller 130 can ramp the TPN solution flow rate signal from a value corresponding to a TPN dose rate of zero to a value corresponding to a continuous phase TPN dose rate. In one embodiment, the flow controller 130 can maintain the insulin solution flow rate signal 124 at a value corresponding to an insulin dose rate of zero during the TPN ramp phase. In another embodiment, the flow controller 130 can maintain the insulin solution flow rate signal 124 as a selected fraction of the TPN solution flow rate signal 122 during the TPN ramp phase to maintain the ratio of the TPN solution to the insulin solution as constant during the TPN ramp phase. In yet another embodiment, the flow controller 130 can maintain the insulin solution flow rate signal 124 at a value corresponding to a continuous phase insulin dose rate during the TPN ramp phase.

The TPN continuous phase can maintain the TPN flow rate through the primary line 112 as constant. An exemplary TPN continuous phase is illustrated at Continuous portion 620 of FIG. 6. Referring to FIG. 1, for the TPN continuous phase the flow controller and can maintain the TPN solution flow rate signal 122 at a value corresponding to a continuous phase TPN dose rate and to maintain the insulin solution flow rate signal 124 at a selected fraction of the TPN solution flow rate signal 122 during the TPN continuous phase. Those skilled in the art will appreciate that the insulin solution flow rate signal 124 can be adjusted during the TPN continuous phase as desired to manually or automatically adjust for measured glucose levels of the patient.

The TPN taper phase can taper the TPN flow rate through the primary line 112 from the TPN flow rate for the TPN continuous phase, such as can be used at the end of the concurrent TPN/insulin infusion. An exemplary TPN taper phase is illustrated at TPN Taper option 306 of FIG. 3A. Referring to FIG. 1, for the TPN taper phase the flow controller can taper the TPN solution flow rate signal 122 from a value corresponding to a continuous phase TPN dose rate to a value corresponding to a TPN dose rate of zero during the TPN taper phase. In one embodiment, the flow controller 130 can maintain the insulin solution flow rate signal 124 at a value corresponding to an insulin dose rate of zero during the TPN taper phase. In another embodiment, the flow controller 130 can maintain the insulin solution flow rate signal 124 as a selected fraction of the TPN solution flow rate signal 122 to maintain the ratio of the TPN solution to the insulin solution as constant during the TPN taper phase. In yet another embodiment, the flow controller 130 can maintain the insulin solution flow rate signal 124 at a value corresponding to a continuous phase insulin dose rate during the TPN taper phase.

The TPN Keep Vein Open (KVO) phase can step the TPN flow rate through the primary line 112 from the TPN flow rate for the TPN continuous phase to zero, such as can be used at the end of the concurrent TPN/insulin infusion. An exemplary TPN KVO phase is illustrated at KVO portion 630 of FIG. 6. Referring to FIG. 1, for the TPN KVO phase the flow controller 130 can decrease the TPN solution flow rate signal 122 from a value corresponding to a continuous phase TPN dose rate to a value corresponding to a Keep Vein Open (KVO) TPN dose rate after a TPN continuous phase. Again, one skilled in the art will recognize in view of the present disclosure that the TPN KVO phase is really just a special case of a Continue at the Same or Different Rate TPN phase.

The insulin flow rate can be adjusted by the user 202 on the fly, i.e., as the concurrent TPN/insulin infusion proceeds, as illustrated in FIGS. 7E-7H. Referring to FIG. 1, the flow controller 130 can vary the insulin solution flow rate signal 124 from a first insulin solution flow rate signal to a second insulin solution flow rate signal in response to input of the second insulin solution flow rate signal by a user 202.

The insulin flow rate can also be adjusted in response to current glucose measurements for the patient 90. The infusion system 100 can also include a glucose sensor 140 operably connected to the patient 90 to monitor glucose level and to provide a glucose signal 92 to the flow controller 130. In one embodiment, the flow controller 130 is further operable to vary the insulin solution flow rate signal 124 from a first insulin solution flow rate signal to a second insulin solution flow rate signal in response to the glucose signal 92. In one embodiment, the glucose sensor 140 can provide the glucose signal 92 to an insulin therapy calculation system or algorithm, which then automatically programs (auto-programs or auto-populates) the flow controller 130 and populates a user interface 200 with updated delivery parameters, such as rate, volume and duration, and the like.

The infusion system 100 can also include a user interface 200 operably connected to the flow controller 130 to provide information for and/or receive instructions from the user 202. The user interface 200 is operable to display a TPN/Insulin Infusion Plot portion having a TPN Infusion profile and an Insulin Infusion profile. An exemplary TPN/Insulin Infusion Plot is illustrated at TPN/Insulin Infusion Plot portion 700 of FIG. 7A. Referring to FIG. 1, in one embodiment, the user interface 200 is further operable to display an Infusion Progression indicator on the TPN/Insulin Infusion Plot portion, the Infusion Progression indicator being operable to indicate a current state of the concurrent TPN/insulin infusion. In one embodiment, the user interface 200 is further operable to display an infusion portion selected from the group consisting of a Ramp portion, a Continuous portion, a Taper portion, and a KVO/continue rate portion. In one embodiment, the user interface 200 is a touch screen. In another embodiment, the user interface 200 is a combination of the electromechanical switches and a graphical display.

FIGS. 2-7 illustrate exemplary screens on the user interface of an infusion system with concurrent TPN/insulin infusion in accordance with the present invention. For clarity of illustration, a hand icon in FIGS. 2-7 indicates interaction of the user 202 with the user interface 200.

Figure 2:
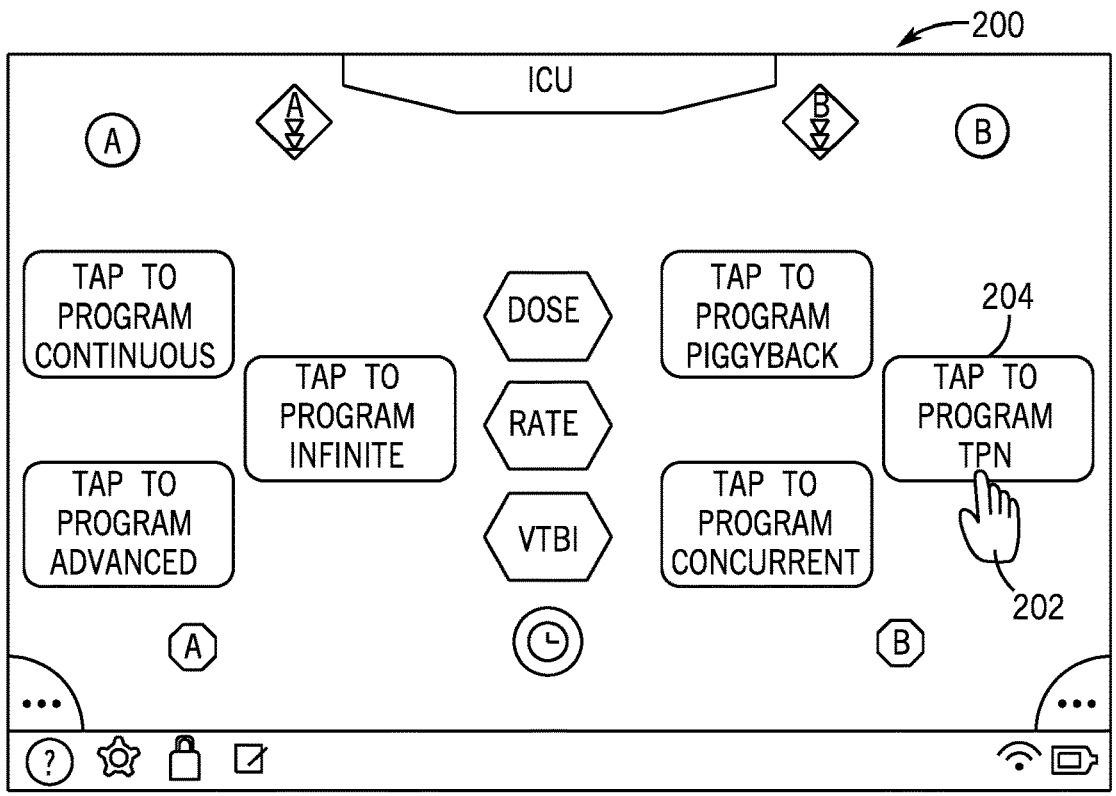
FIG. 2 is an operating mode option screen for an infusion system with concurrent TPN/insulin infusion in accordance with the present invention.

FIG. 2 is an operating mode option screen for an infusion system with concurrent TPN/insulin infusion in accordance with the present invention. The user 202 can select Tap to Program TPN key 204 on the user interface 200 to initiate programming of a concurrent TPN/insulin infusion.

Figure 3A:
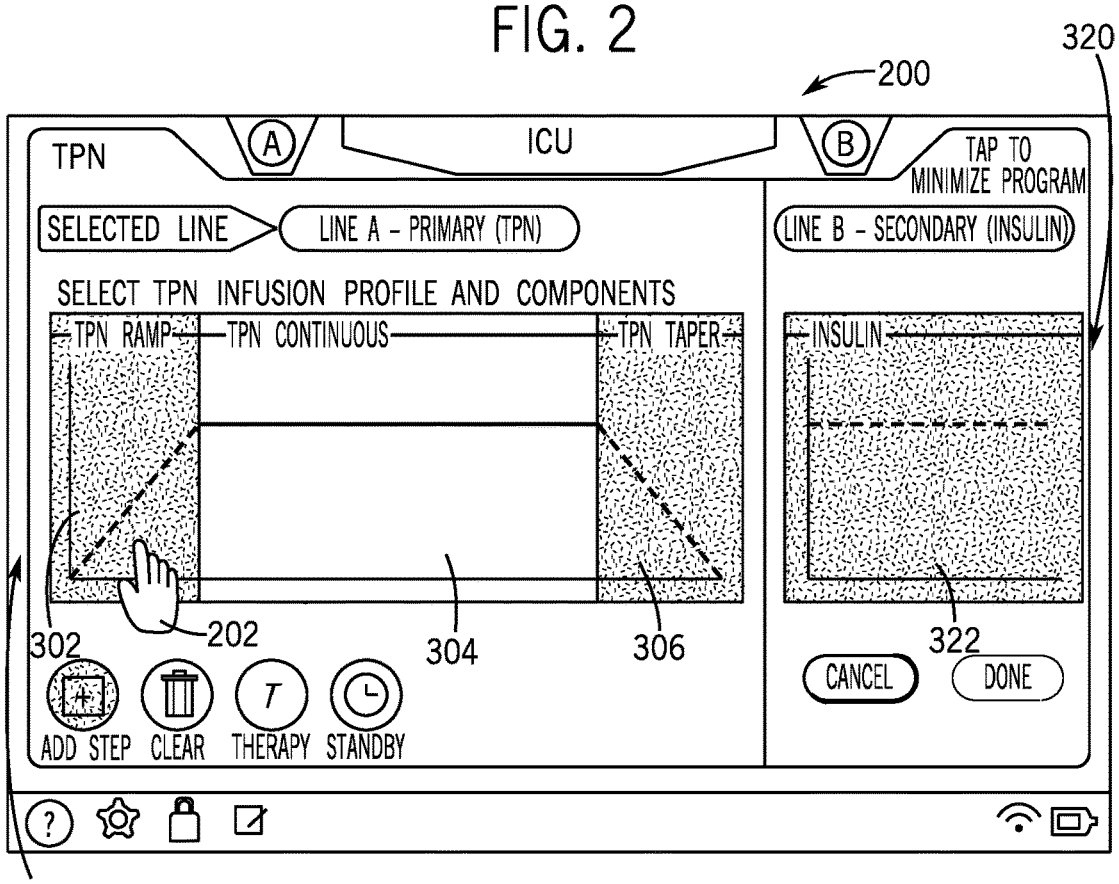
FIGS. 3A-3C are infusion profile selection screens for an infusion system with concurrent TPN/insulin infusion in accordance with the present invention.
Figure 3B:
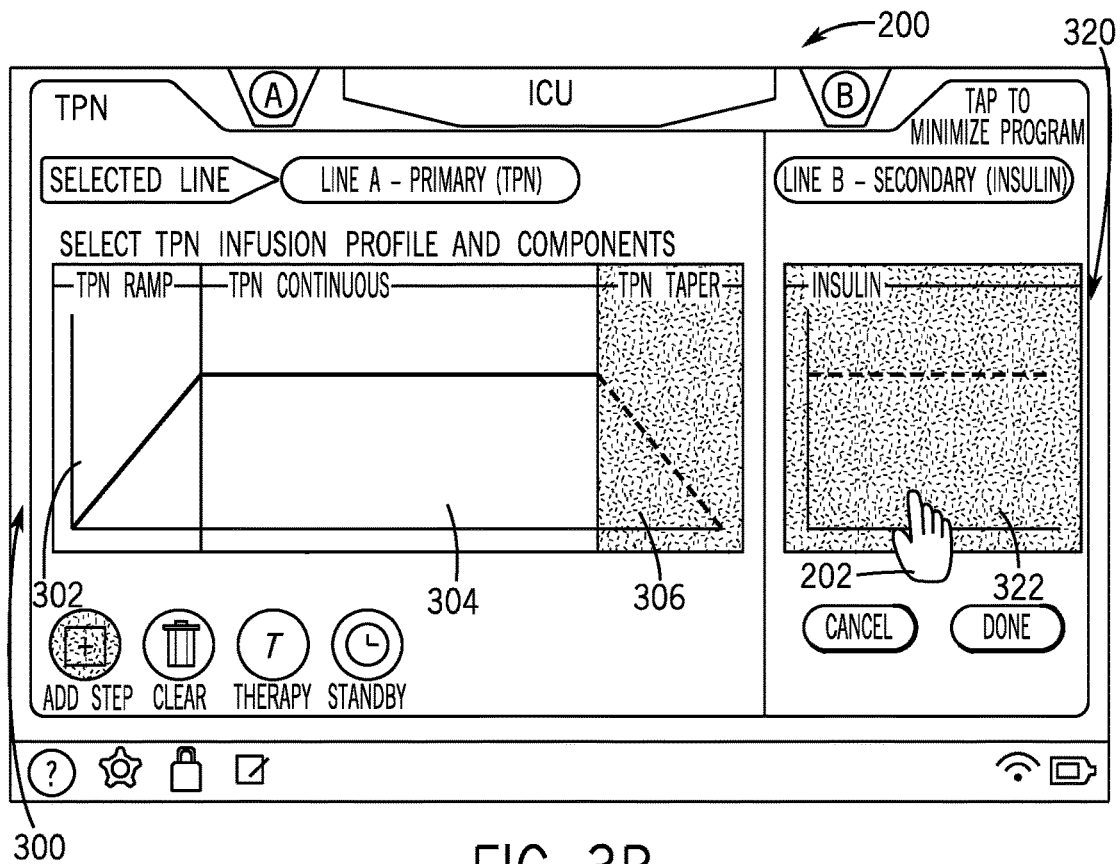
Figure 3C:
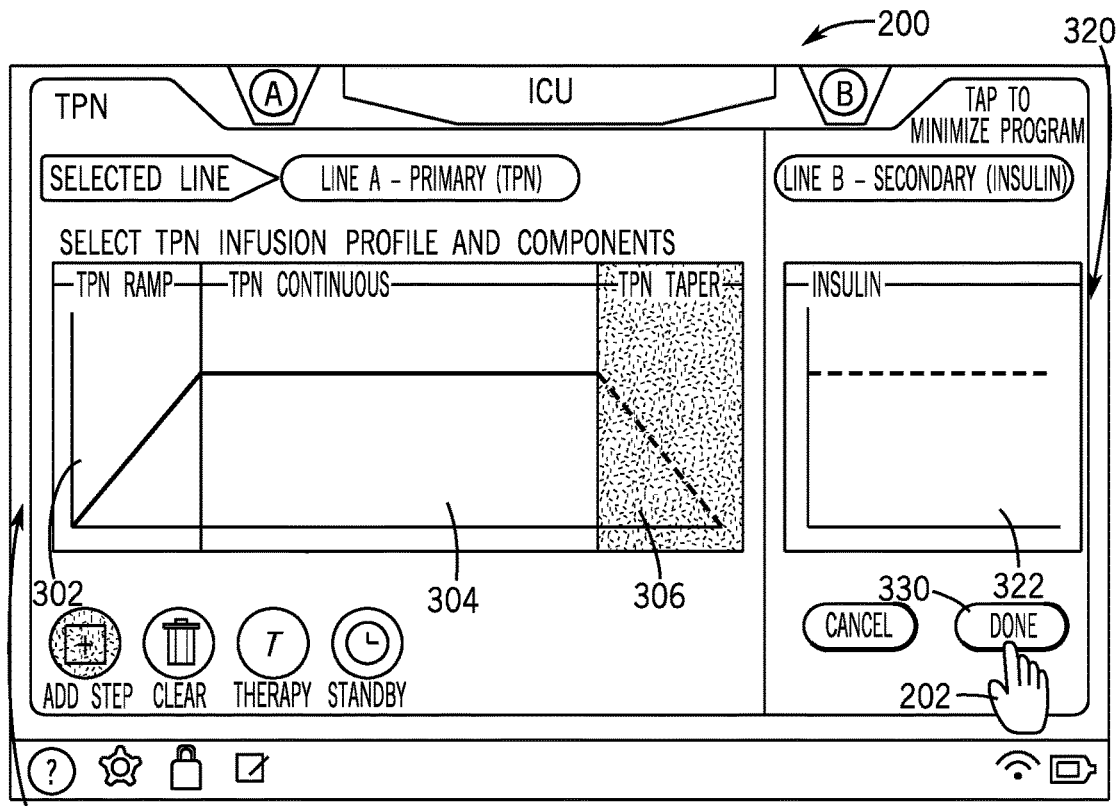

FIGS. 3A-3C are infusion profile selection screens for an infusion system with concurrent TPN/insulin infusion in accordance with the present invention. The user can select a desired profile for concurrent TPN/insulin infusion.

Referring to FIG. 3A, the user interface 200 displays a TPN portion 300 for selecting the TPN infusion profile and an insulin portion 320 for selecting concurrent insulin infusion. In this example, the TPN portion 300 is associated with the primary line A and the insulin portion 320 is associated with the secondary line B. The TPN portion 300 can include a TPN Ramp option 302, a TPN Continuous option 304, and a TPN Taper option 306. The insulin portion 320 can include an Infusion option 322. In this example, the TPN Continuous option 304 is selected by default, and the TPN Ramp option 302, the TPN Taper option 306, and the Infusion option 322 are unselected. The user 202 selects the TPN Ramp option 302 and leaves the TPN Taper option 306 unselected. In this example, the unselected options are grayed out and the selected options are highlighted on the user interface 200.

In one embodiment, the TPN continuous option 304 is selected by default so that the user does not have to select the TPN continuous option 304. In one embodiment, the TPN Ramp option 302, the TPN Taper option 306, and the Infusion option 322 are unselected by default. Those skilled in the art will appreciate that the selected an unselected options can be provided in any combination as desired for a particular application.

Referring to FIG. 3B, the user 202 selects the Infusion option 322 in the infusion portion 320. Referring to FIG. 3C, the user 202 has completed selection of the concurrent TPN/insulin infusion profile and selects a Done key 330 to close out the profile selection and proceed to TPN infusion setup. The TPN Ramp option 302, the TPN Continuous option 304, and the Infusion option 322 are enabled as indicated by the highlighting.

FIGS. 4A-4I are TPN infusion setup screens for an infusion system with concurrent TPN/insulin infusion in accordance with the present invention.

Figure 4A:
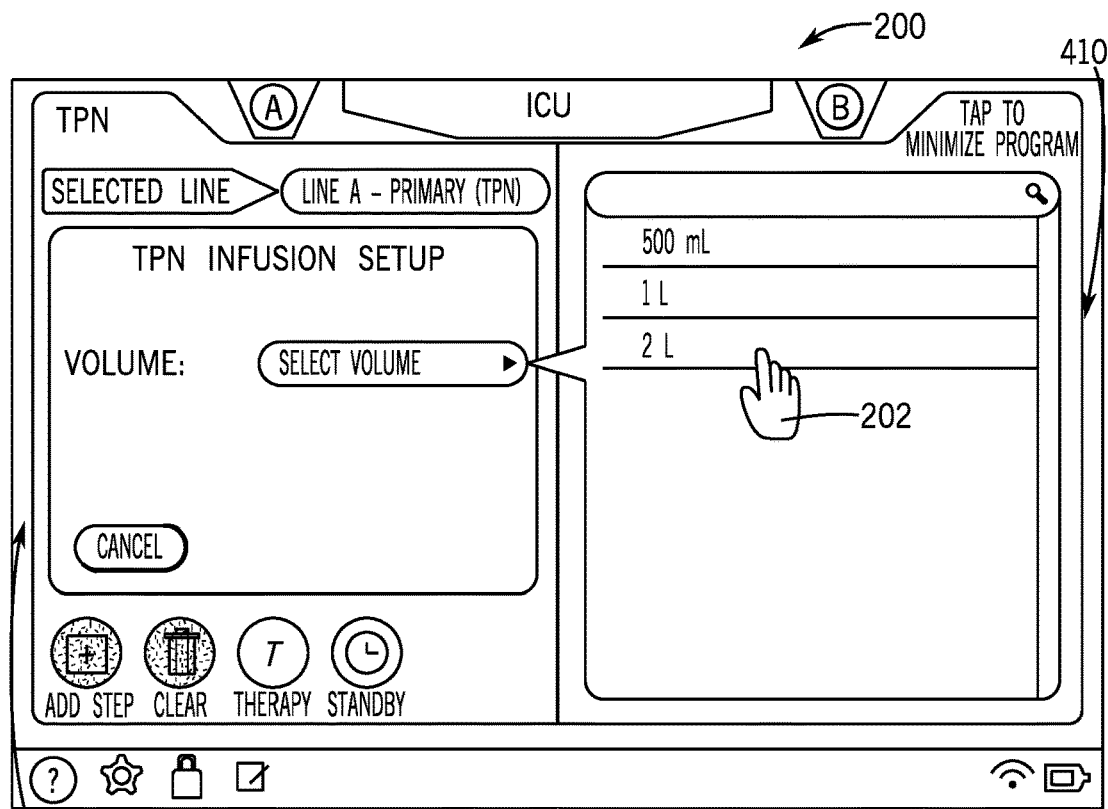
FIGS. 4A-4I are TPN infusion setup screens for an infusion system with concurrent TPN/insulin infusion in accordance with the present invention.

Referring to FIG. 4A, the user interface 200 displays a TPN Infusion Setup portion 380 and a TPN Volume portion 410 displaying potential volumes of TPN solution available for selection, i.e., potential TPN solution container volumes. In this example, the user 202 selects 2 L as the TPN solution volume to match the TPN solution container volume of the TPN source connected to the disposable cassette.

Figure 4B:
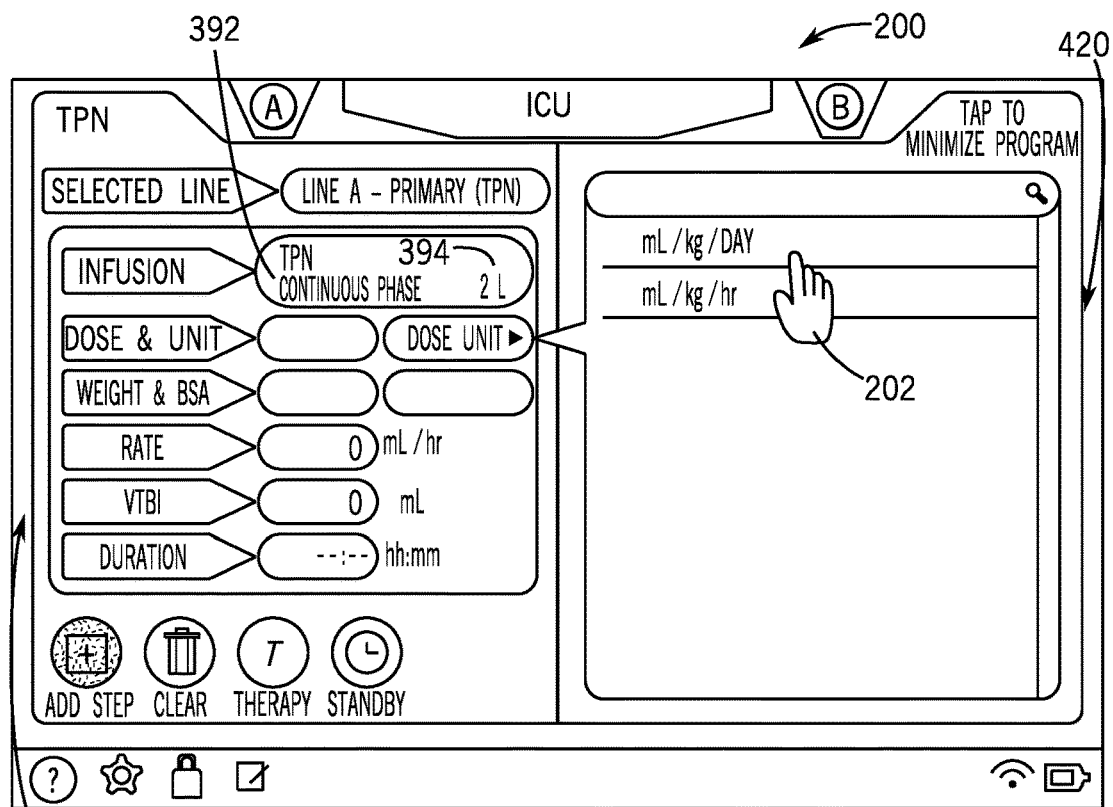

Referring to FIG. 4B, the user interface 200 displays a TPN Continuous Phase portion 390 and a TPN Dose Unit portion 420. The TPN Continuous Phase portion 390 includes a TPN Phase Being Programmed indicator 392 and a TPN Solution Volume indicator 394. The TPN Dose Unit portion 420 displays potential dose units for selection. In this example, the user 202 selects mL/kg/day as the dose unit.

Figure 4C:
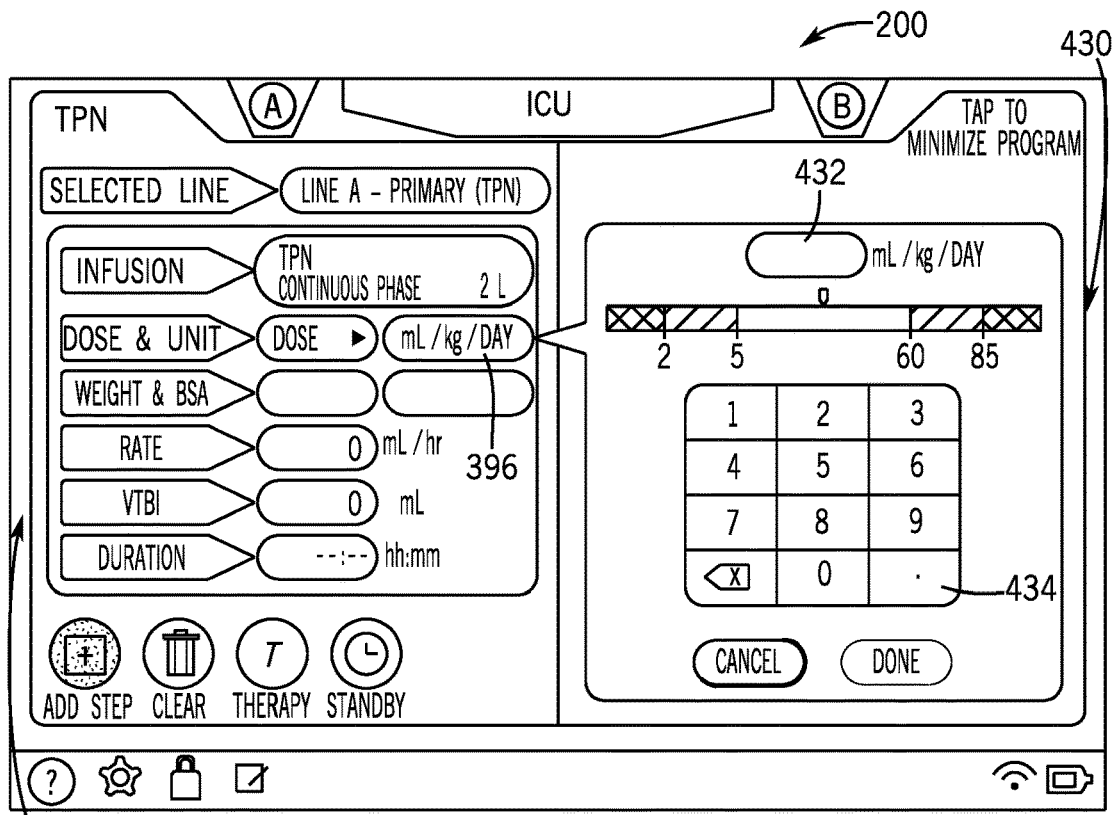
Figure 4D:
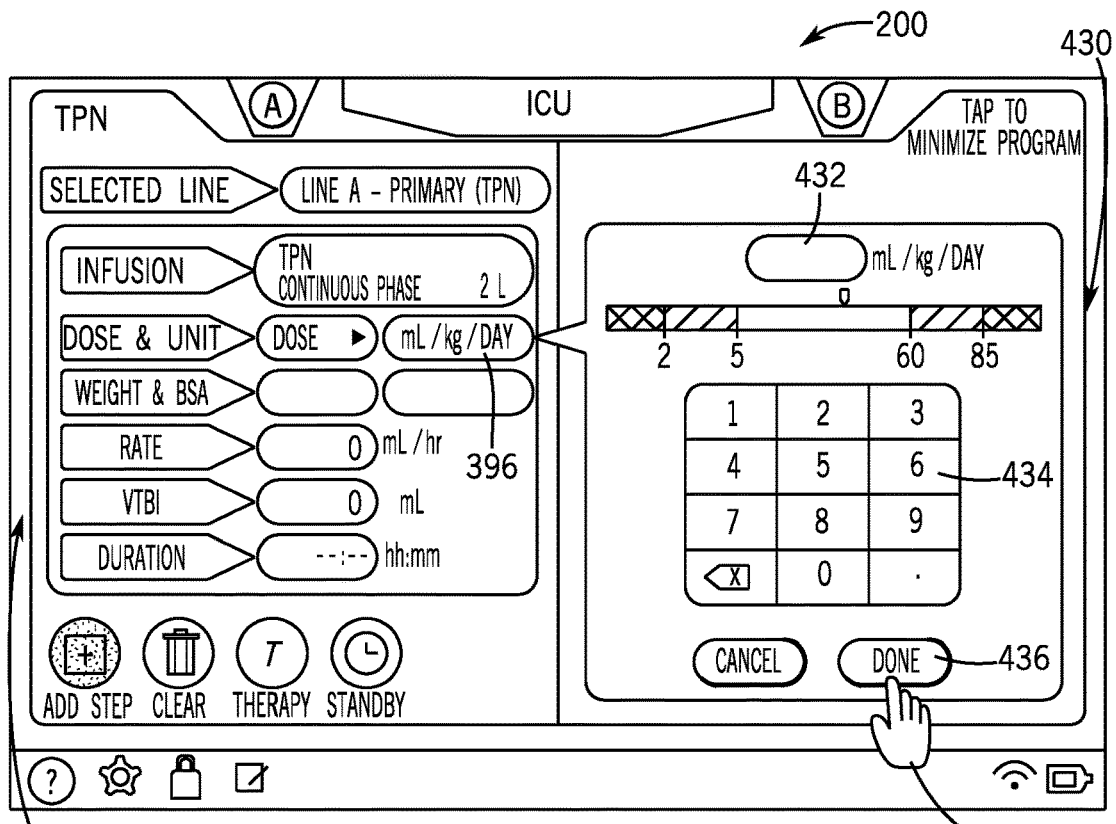

Referring to FIG. 4C, the user interface 200 displays a TPN Dose Unit indicator 396 in the TPN Continuous Phase portion 390, and a Desired TPN Dose box 432 and entry keypad 434 in the TPN Dose portion 430. The user can enter the desired TPN dose to be delivered during the TPN continuous phase in the Desired TPN Dose box 432 using the entry keypad 434. Referring to FIG. 4D, the desired TPN dose appears in the Desired TPN Dose box 432 and the user 202 selects a Done key 436 to close out the TPN Dose & Unit selection and proceed to a Weight selection.

Figure 4E:
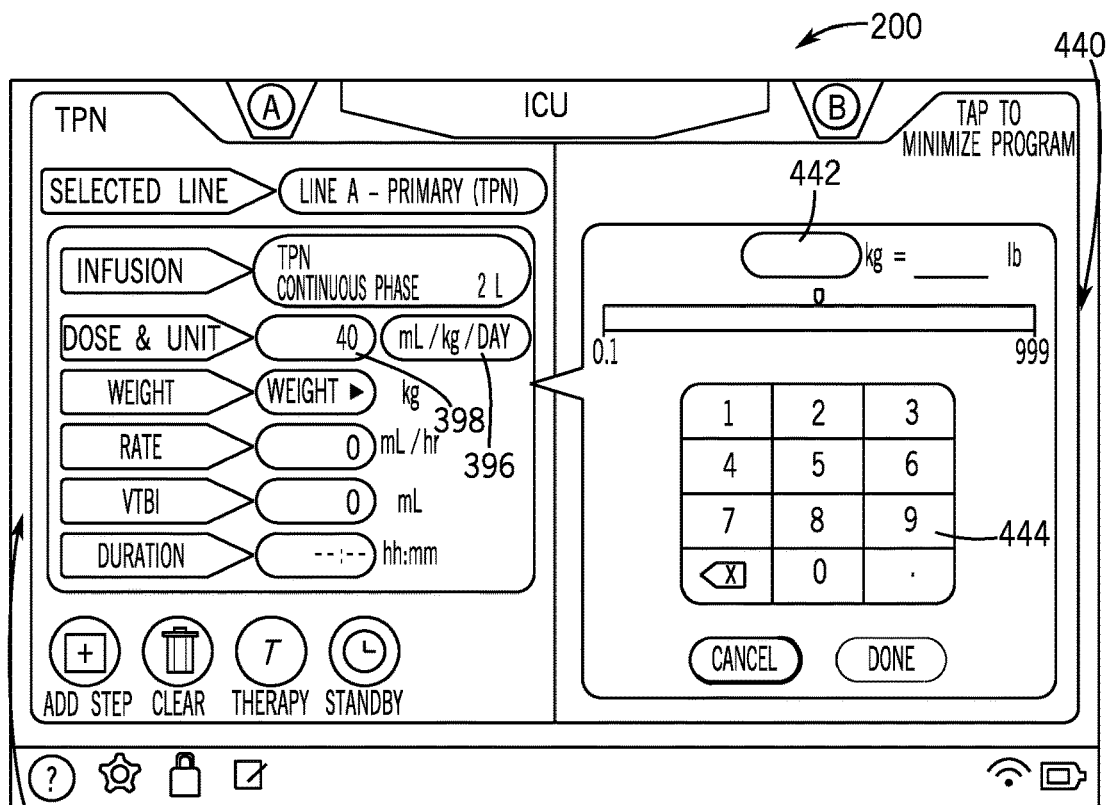
Figure 4F:
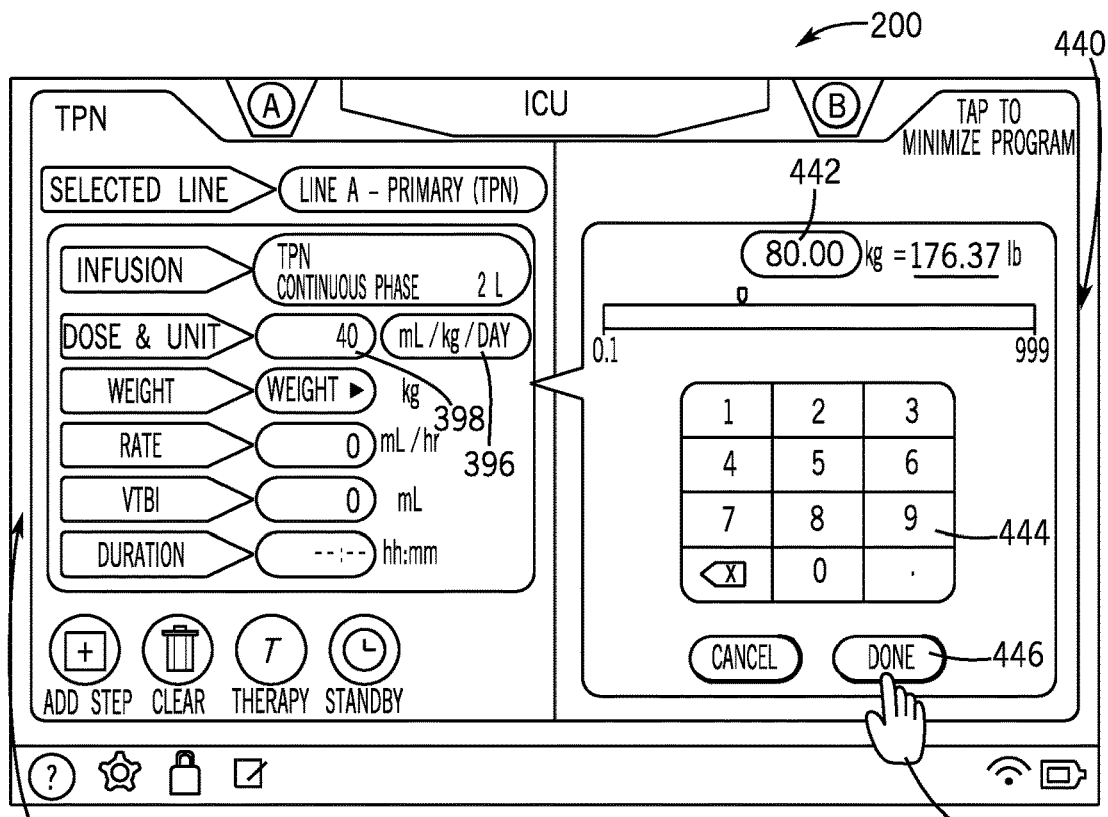

Referring to FIG. 4E, the user interface 200 displays a TPN Dose indicator 398 in the TPN Continuous Phase portion 390, and a Weight box 442 and entry keypad 444 in the TPN Dose Unit portion 440. The user can enter the weight of the patient in the Weight box 442 using the entry keypad 444. Referring to FIG. 4F, the weight appears in the Weight box 442 and the user 202 selects a Done key 446 to close out the Weight selection and proceed to TPN Duration selection.

Figure 4G:
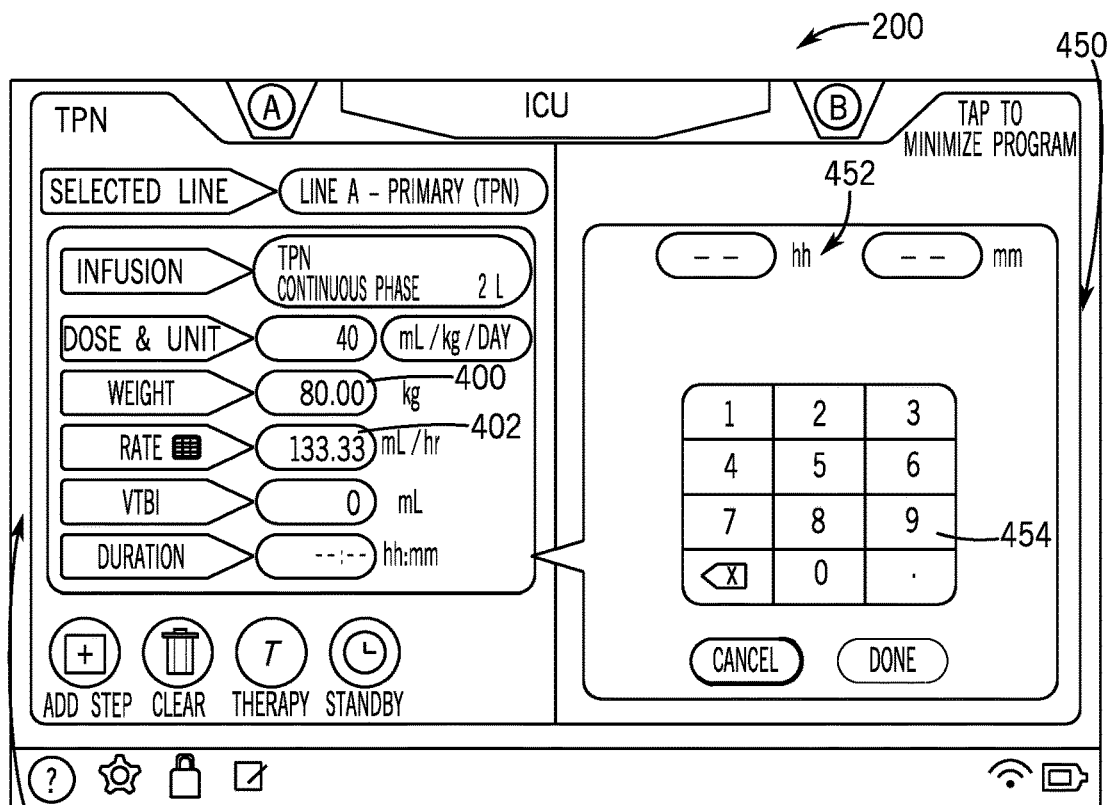
Figure 4H:
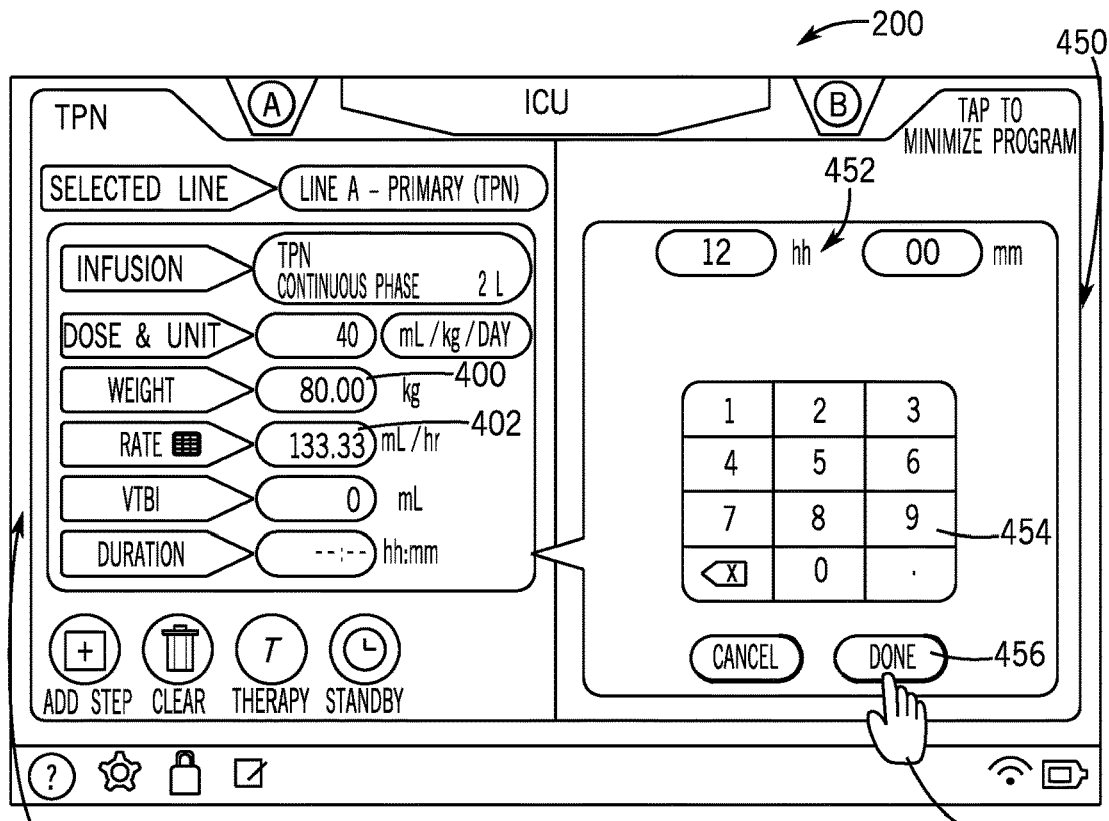

Referring to FIG. 4G, the user interface 200 displays a Weight indicator 400 and a TPN Rate indicator 402 in the TPN Continuous Phase portion 390. The numerical value for the rate in the TPN Rate indicator 402 is automatically calculated based on the dose, dose unit, and weight. The user interface 200 also displays a TPN Duration box 452 and entry keypad 454 in the TPN Dose Unit portion 450. The user can enter the desired TPN dose duration of the TPN continuous phase the TPN Duration box 452 using the entry keypad 454. Referring to FIG. 4H, the desired TPN dose appears in the TPN Duration box 452 and the user 202 selects a Done key 456 to close out the TPN Duration selection and proceed to TPN Options selection.

Figure 4I:
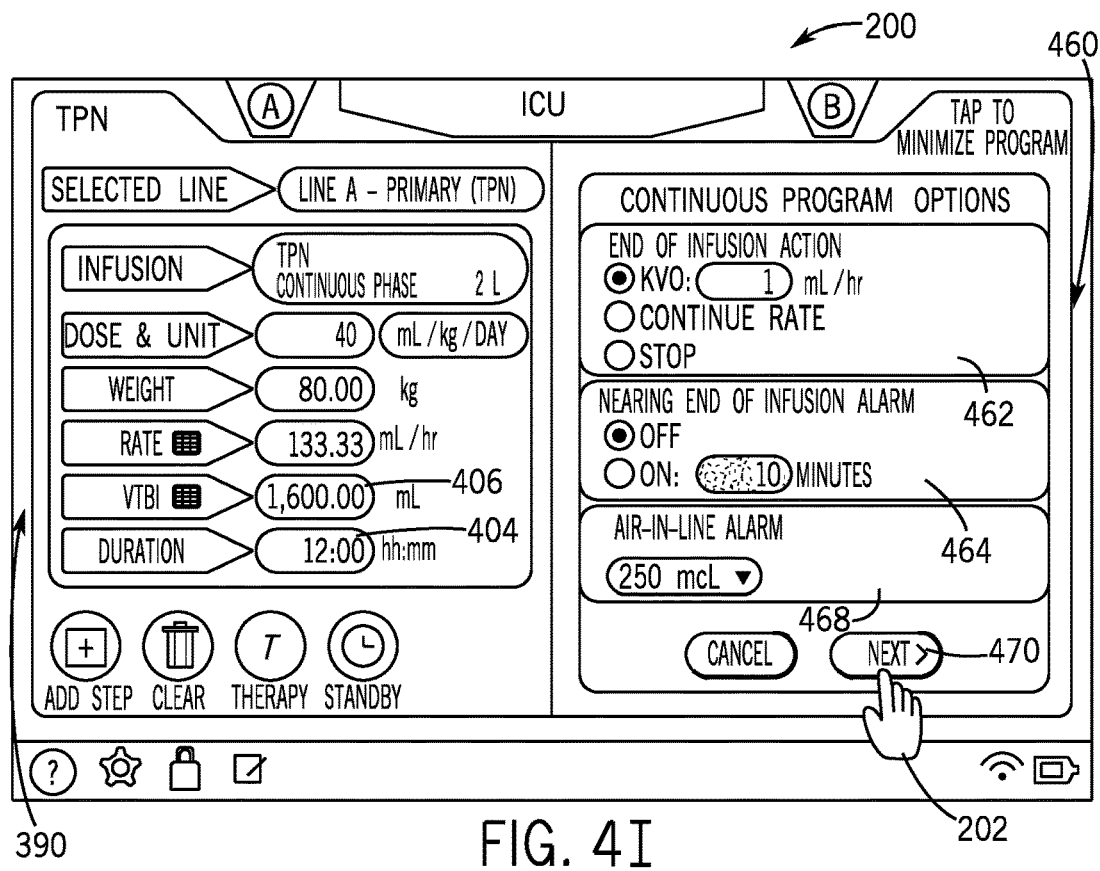

Referring to FIG. 4I, the user interface 200 displays a TPN Duration indicator 404 and a TPN Volume to Be Infused (VTBI) indicator 406 in the TPN Continuous Phase portion 390. The numerical value for the VTBI in the VTBI indicator 406 is automatically calculated based on the duration and rate. The user interface 200 also displays a TPN Continuous Program Options portion 460 including an End of Infusion Action section 462, a Nearing End of Infusion Alarm section 464, and an Air-in-Line Alarm section 468. The End of Infusion Action section 462 includes options to be performed after the TPN infusion is complete, such as a Keep Vein Open (KVO) option with rate value input to continue infusion at a reduced rate, a Continue Rate option to continue infusion at the previous rate, and a Stop option to end the infusion. In this example, the Keep Vein Open (KVO) option with a rate value of one mL/hr is selected. The Nearing End of Infusion Alarm section 464 includes enabling or disabling (On or Off) an optional alarm as the TPN infusion nears completion, with a value time input for the amount of time before the End of Infusion alarm is to occur. In this example, the Nearing End of Infusion Alarm is turned off. The Air-in-Line Alarm section 468 provides an air volume input value at which the Air-in-Line Alarm is to occur. In this example, the Air-in-Line Alarm is set to occur at an error volume of 250 mcL. The user 202 selects a Next key 470 to close out the Options selection and proceed to insulin infusion setup.

FIGS. 5A-5F are insulin infusion setup screens for an infusion system with concurrent TPN/insulin infusion in accordance with the present invention.

Figure 5A:
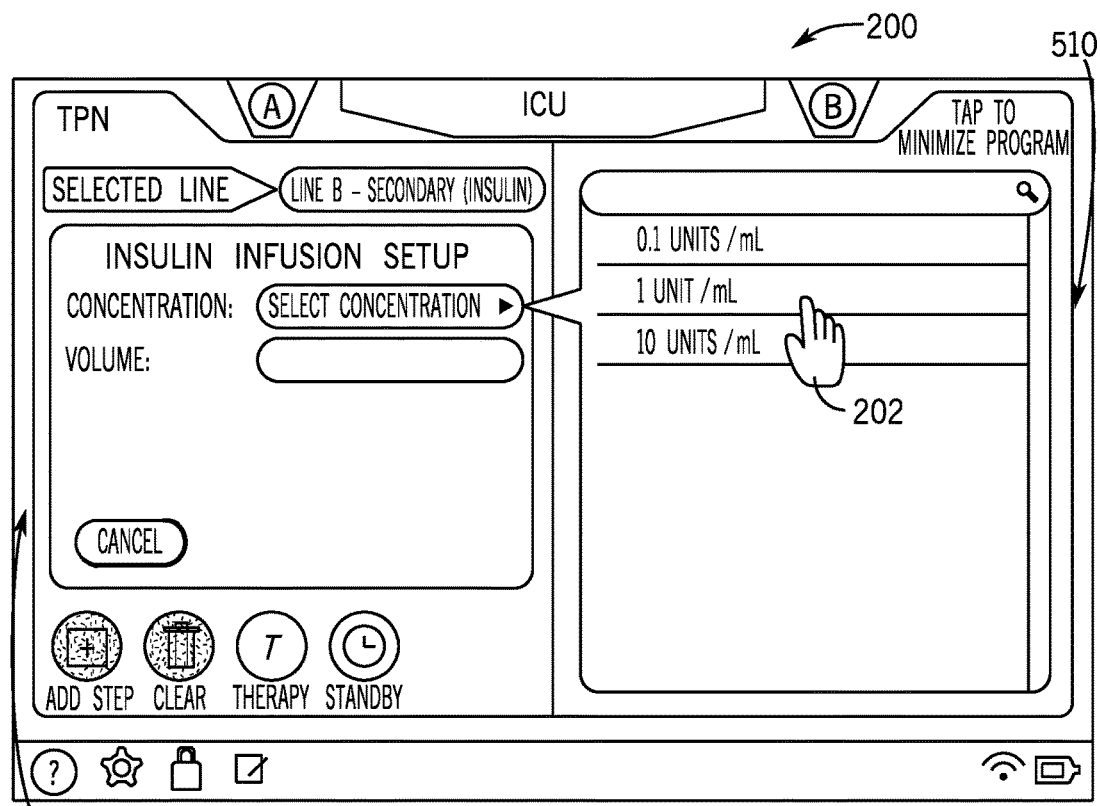
FIGS. 5A-5F are insulin infusion setup screens for an infusion system with concurrent TPN/insulin infusion in accordance with the present invention.

Referring to FIG. 5A, the user interface 200 displays an Insulin Infusion Setup portion 480 and an Insulin Concentration portion 510 displaying potential concentrations of insulin solution available for selection. In this example, the user 202 selects 1 unit/mL concentration as the insulin solution concentration.

Figure 5B:
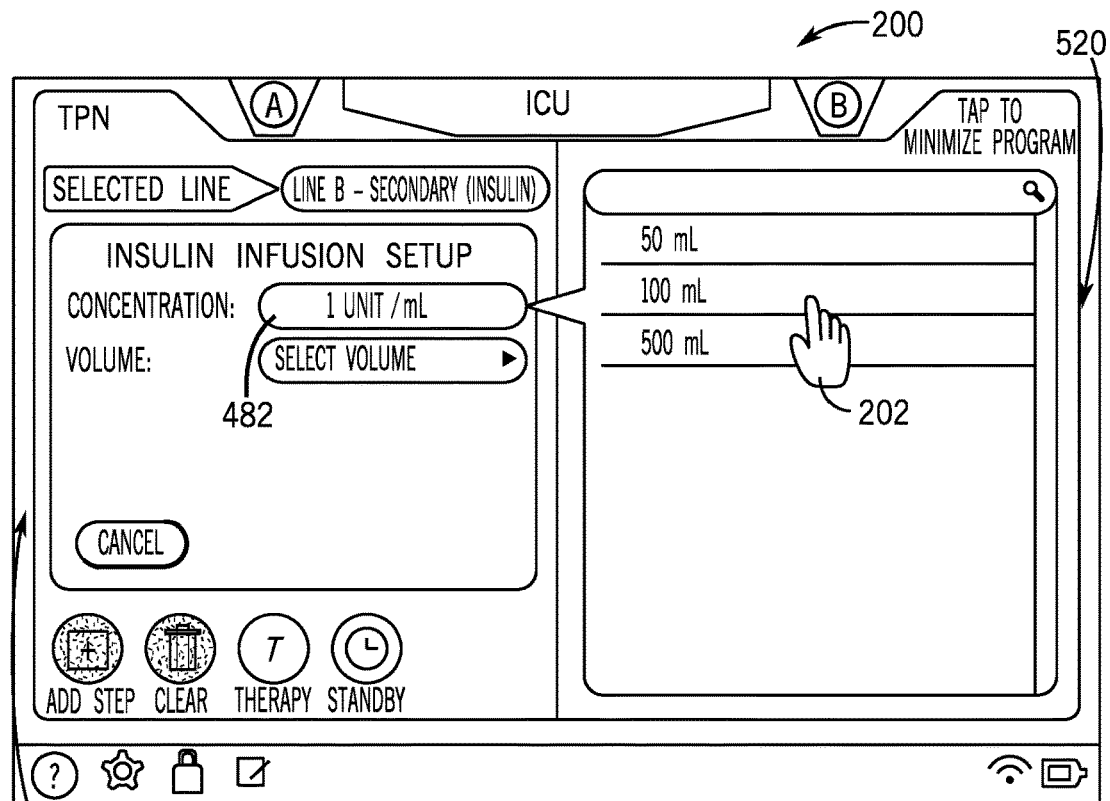

Referring to FIG. 5B, the user interface 200 displays an Insulin Solution Concentration indicator 482 in the Insulin Infusion Setup portion 480 and potential volumes of insulin solution available for selection, i.e., potential insulin solution container volumes, in an Insulin Volume portion 520. In this example, the user interface 200 switches from the Insulin Concentration portion to the Insulin Volume portion 520 automatically when the user selects the insulin solution concentration in the Insulin Concentration portion. In this example, the user 202 selects a 100 mL as the insulin solution volume to match the insulin solution container volume of the insulin source connected to the disposable cassette.

Figure 5C:
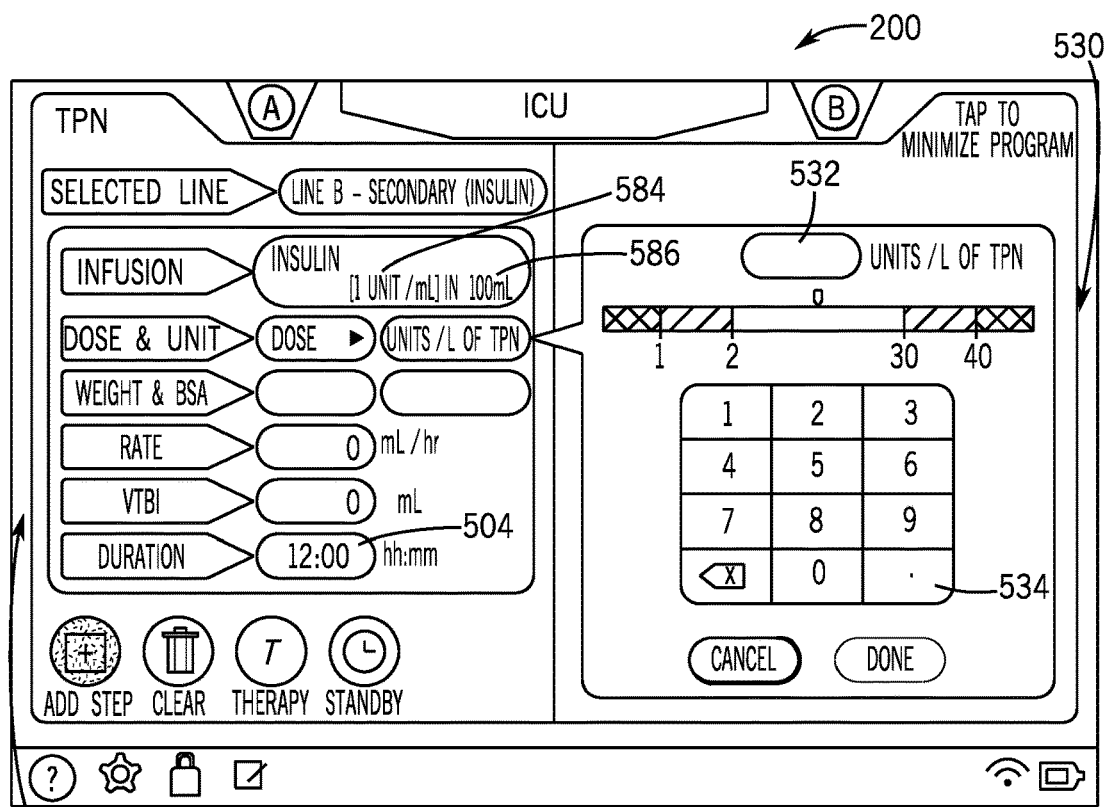
Figure 5D:
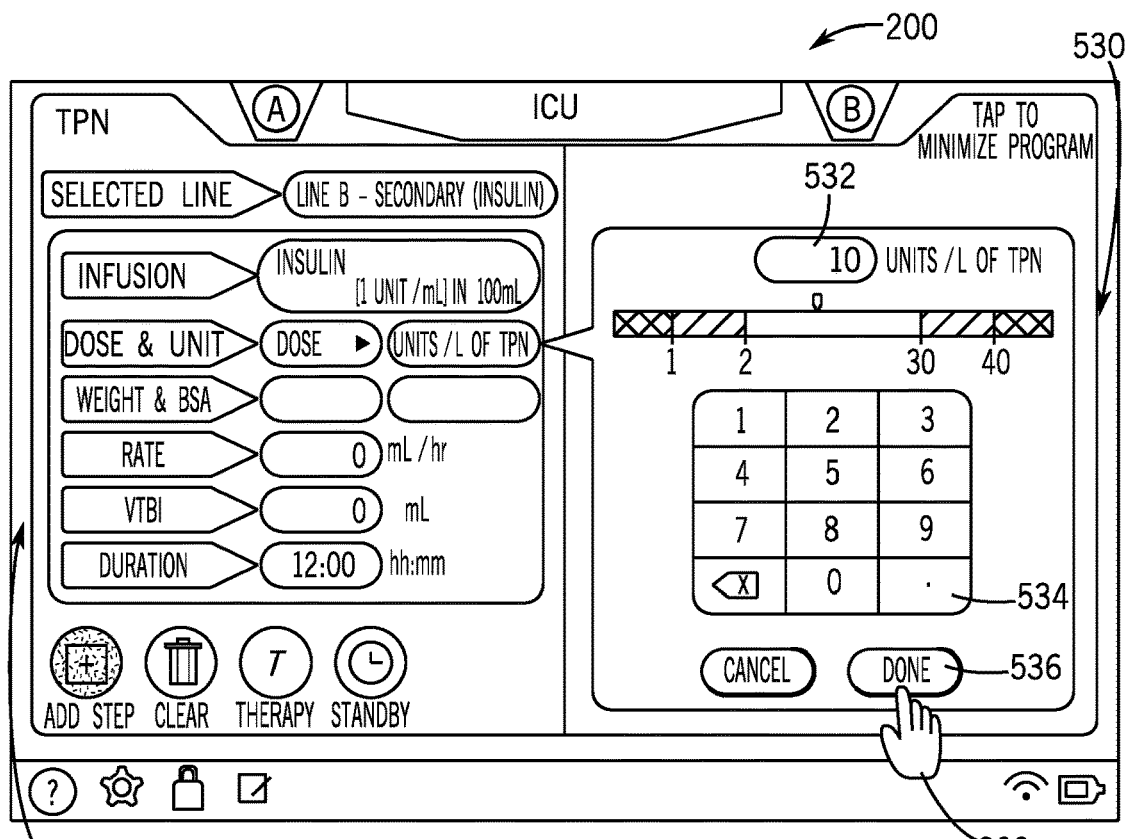

Referring to FIG. 5C, the user interface 200 displays an Insulin Solution Concentration indicator 584 and an Insulin Solution Volume indicator 586 in an Insulin Infusion portion 490, which also includes the Insulin Duration indicator 504 showing the previously entered desired TPN dose duration (being the same as the desired insulin dose duration). The user interface 200 also displays a Desired Insulin Dose box 532 and entry keypad 534 in the Insulin Dose portion 530. The dose units are automatically selected to be the standard Units (of insulin)/L of TPN. The user can enter the desired insulin dose to be delivered during the TPN continuous phase in the Desired Insulin Dose box 532 using the entry keypad 534. Referring to FIG. 5D, the desired insulin dose appears in the Desired Insulin Dose box 532 and the user 202 selects a Done key 536 to close out the Insulin Dose & Unit selection and proceed to Insulin Options selection.

Figure 5E:
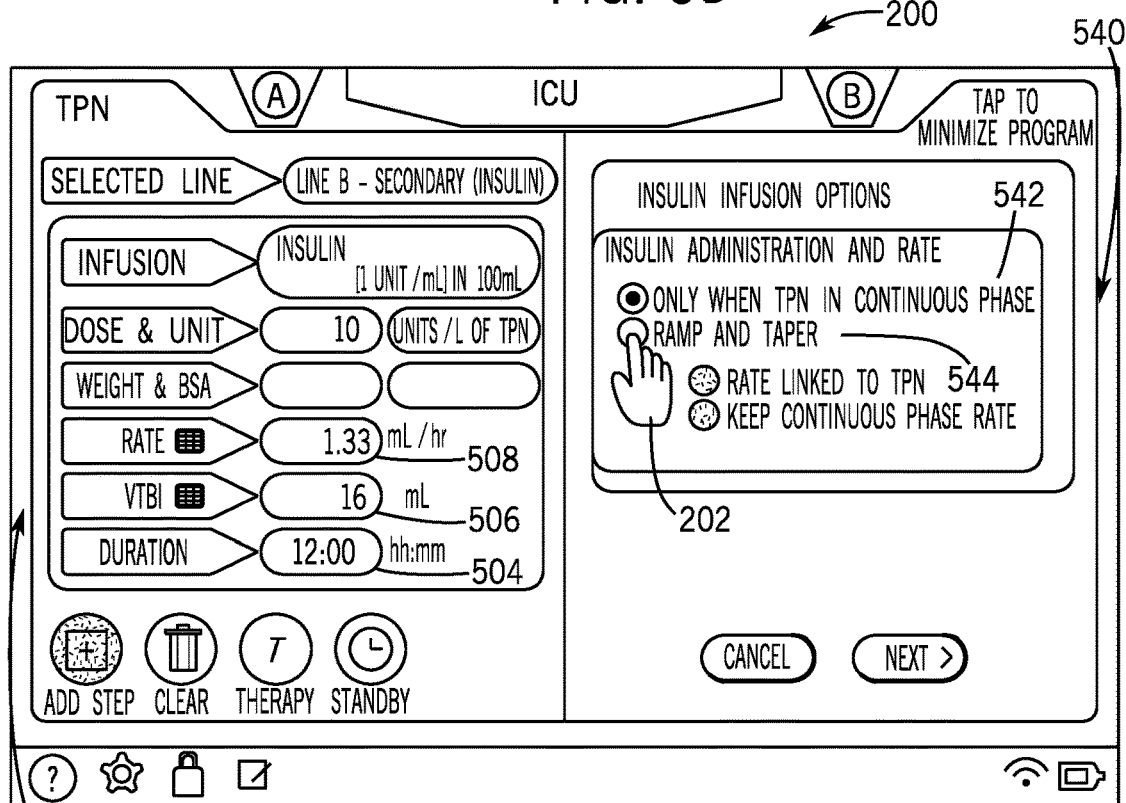
Figure 5F:
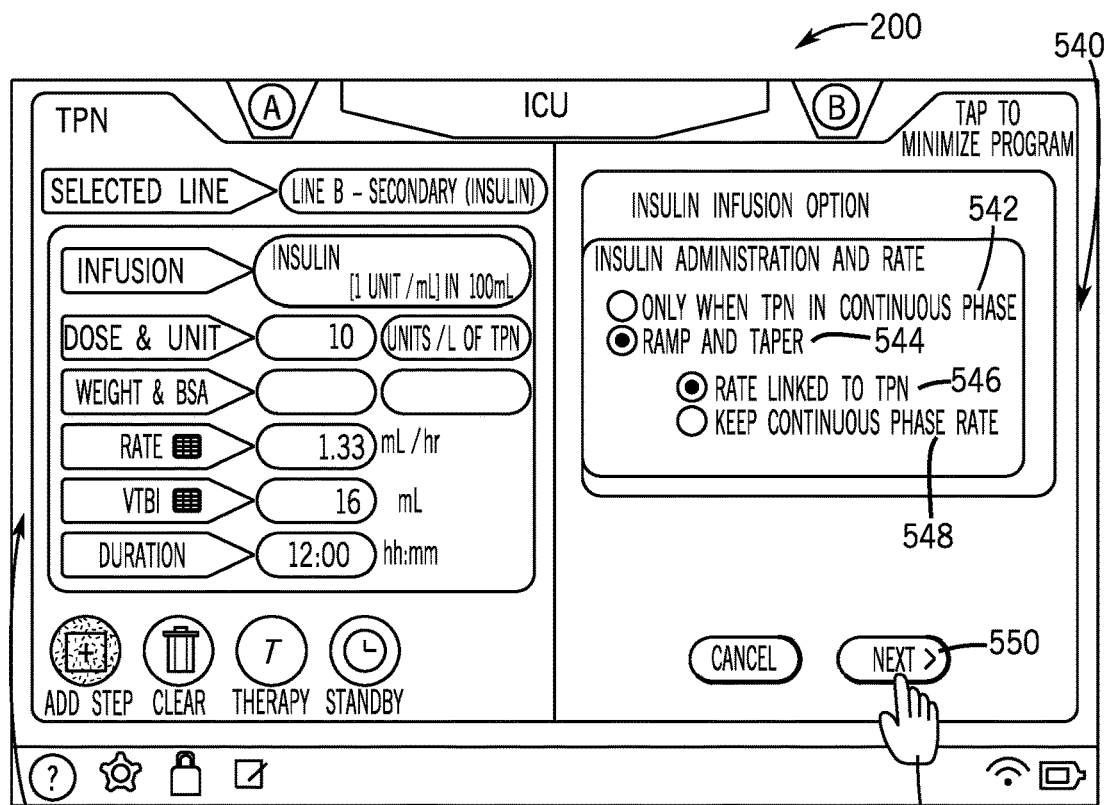

Referring to FIG. 5E, the user interface 200 displays an Insulin Volume to Be Infused (VTBI) indicator 506 and an Insulin Rate indicator 508 in the Insulin Continuous Phase portion 490. The insulin VTBI and insulin rate are automatically calculated from the insulin duration, the TPN VTBI, and the TPN rate entered and/or calculated previously. The user interface 200 also displays an Insulin Infusion Options portion 540 providing additional options for insulin administration and rate. The insulin infusion options allow independently titrating the insulin delivery or linking the insulin delivery to the TPN delivery in ways that cannot be achieved if the TPN solution and insulin solution are premixed in the same IV bag. When the Only When TPN in Continuous Phase button 542 is selected, insulin infusion is only provided when the TPN is in the continuous phase. In this example, the user 202 is selecting the Ramp and Taper button 544.

Referring to FIG. SF, the Ramp and Taper button 544 is selected and the Only When TPN in Continuous Phase button 542 is deselected. During the ramp and taper portion of the infusion, the insulin infusion rate can be linked to the TPN infusion rate by selecting a Rate Linked to TPN button 546 or can be maintained at the insulin infusion rate used in the TPN continuous phase by selecting the Keep Continuous Phase Rate button 548. In this example, the Rate Linked to TPN button 546 is selected. The user 202 selects a Next key 550 to close out the Insulin Infusion Options selection and proceed to infusion confirmation.

Figure 6:
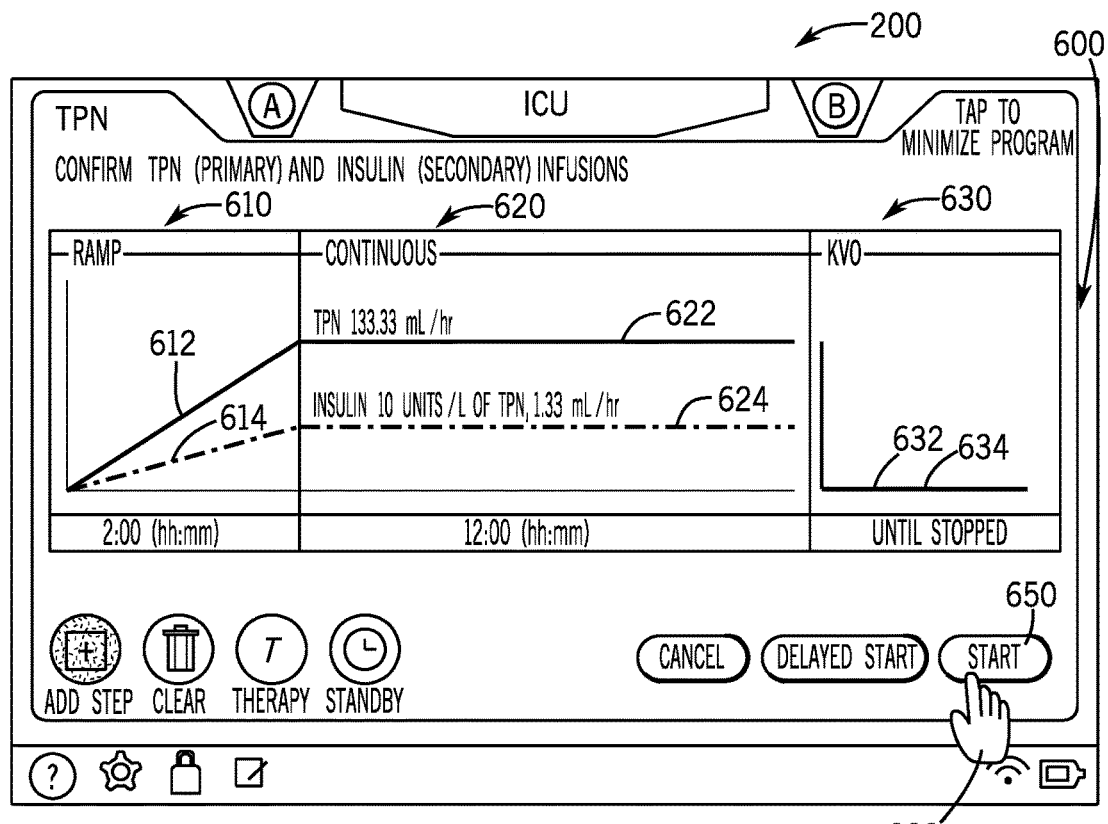
FIG. 6 is a confirmation screen for an infusion system with concurrent TPN/insulin infusion in accordance with the present invention.

FIG. 6 is a confirmation screen for an infusion system with concurrent TPN/insulin infusion in accordance with the present invention. The user can check the confirmation screen to verify that the TPN infusion parameters and insulin infusion parameters have been entered and calculated as desired.

The user interface 200 displays a confirmation screen 600 having a Ramp portion 610, a Continuous portion 620, and a KVO portion 630. The confirmation screen 600 further includes TPN infusion profiles 612, 622, 632 and insulin infusion profiles 614, 624, 634. In this example based on the previously entered parameters, the TPN infusion ramp 612 increases from zero to 133.33 mL/hr over 2.0 hours. The insulin infusion ramp 614, linked to the TPN infusion, increases from zero to 1.33 mL/hr over 2.0 hours. In this example, ramping is preset to 2 hours, but can also be altered as needed for a particular application. For the next 12 hours after the infusion ramp, the TPN continuous infusion 622 is maintained at 133.33 mL/hr and the insulin continuous infusion 624 is maintained at 1.33 mL/hr. Until stopped after the continuous infusion, the TPN KVO infusion 632 is maintained at 1.0 mL/hr and the insulin KVO infusion 634 is zero. The user 202 selects a Start key 650 to start the concurrent TPN/insulin infusion.

FIGS. 7A-7J are operational screens for an infusion system with concurrent TPN/insulin infusion in accordance with the present invention. The operational screens display numerical and graphical information for the concurrent TPN/insulin infusion as planned and as the infusion proceeds.

Figure 7A:
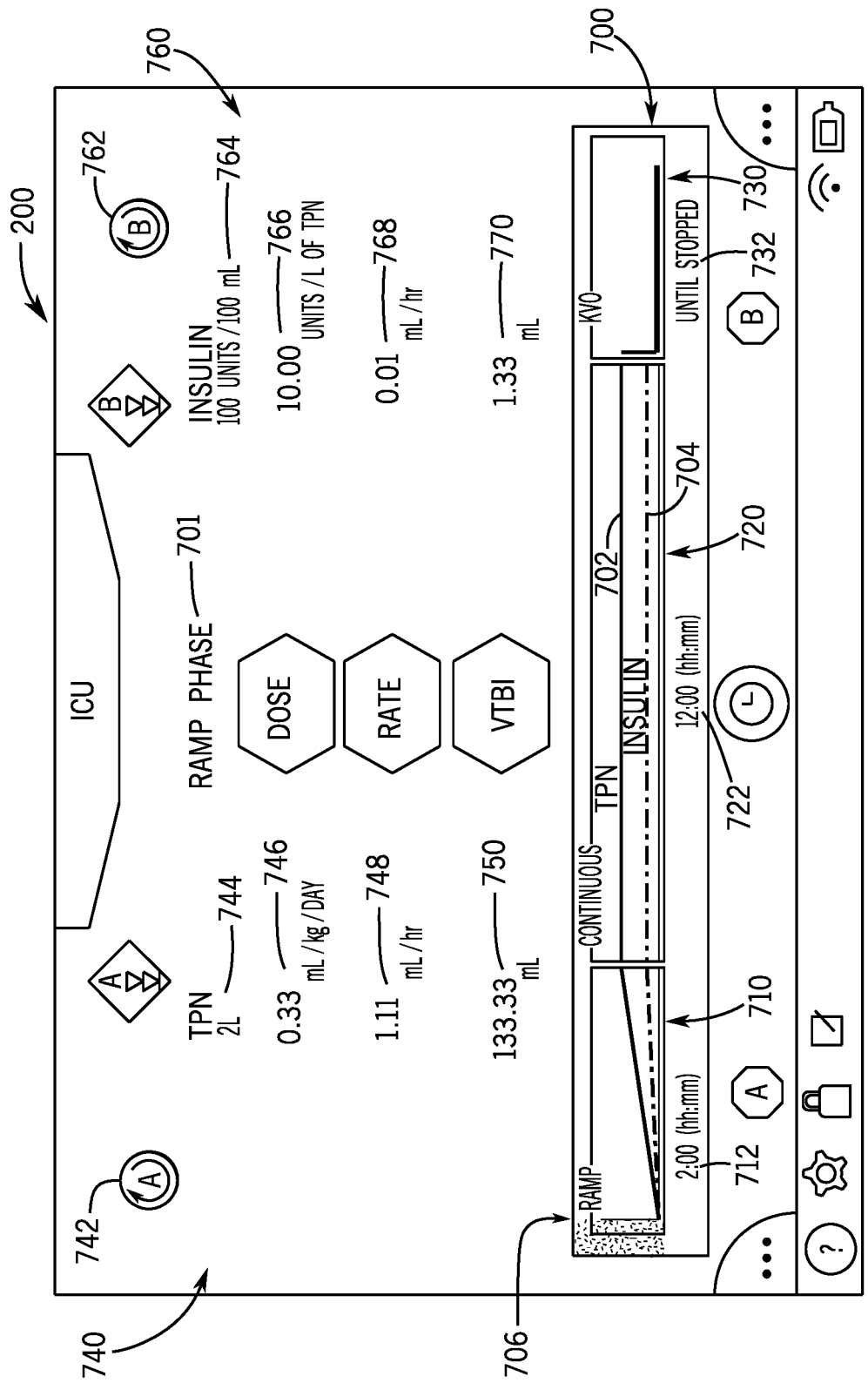
FIGS. 7A-7J are operational screens for an infusion system with concurrent TPN/insulin infusion in accordance with the present invention.

Referring to FIG. 7A, the user interface 200 displays an Infusion Phase indicator 701, a TPN/Insulin Infusion Plot portion 700, a TPN Infusion portion 740, and an Insulin Infusion portion 760. The Infusion Phase indicator 701 displays the current phase of the concurrent TPN/insulin infusion.

The TPN/Insulin Infusion Plot of the TPN/Insulin Infusion Plot portion 700 displays infusion profiles and visual status for two concurrent drug deliveries. The TPN/Insulin Infusion Plot portion 700 has a Ramp portion 710 with a Ramp Phase Time Remaining indicator 712, a Continuous portion 720 with a Continuous Phase Time Remaining indicator 722, and a KVO portion 730 with a KVO Phase Time Remaining indicator 732. A TPN Infusion profile 702 and an Insulin Infusion profile 704 display the injection rates of the TPN infusion and Insulin Infusion with time over the concurrent TPN/insulin infusion. An Infusion Progression indicator 706 illustrates the current state of the concurrent TPN/insulin infusion. In this example, the TPN/Insulin Infusion Plot portion 700 preceding the Infusion Progression indicator 706 is grayed out.

The TPN Infusion portion 740 includes a Line A Activity indicator 742 (which can be animated to indicate that the Line A is pumping), a TPN Solution Volume indicator 744, a TPN Dose indicator 746, a TPN Dose Rate indicator 748, and a TPN VTBI indicator 750. The Insulin Infusion portion 760 includes a Line B Activity indicator 762 (which can be animated to indicate that the Line A is pumping), an Insulin Solution Volume indicator 764, an Insulin Dose indicator 766, an Insulin Rate indicator 768, and an Insulin VTBI indicator 770. The values presented in the TPN Infusion portion 740 and the Insulin Infusion portion 760 are updated as the concurrent TPN/insulin infusion proceeds. The values illustrated in the example of FIG. 7A are at the beginning of the ramp phase of the concurrent TPN/insulin infusion. The infusion rate of each line will gradually ramp over the next 2 hours until the continuous phase is reached.

Figure 7B:
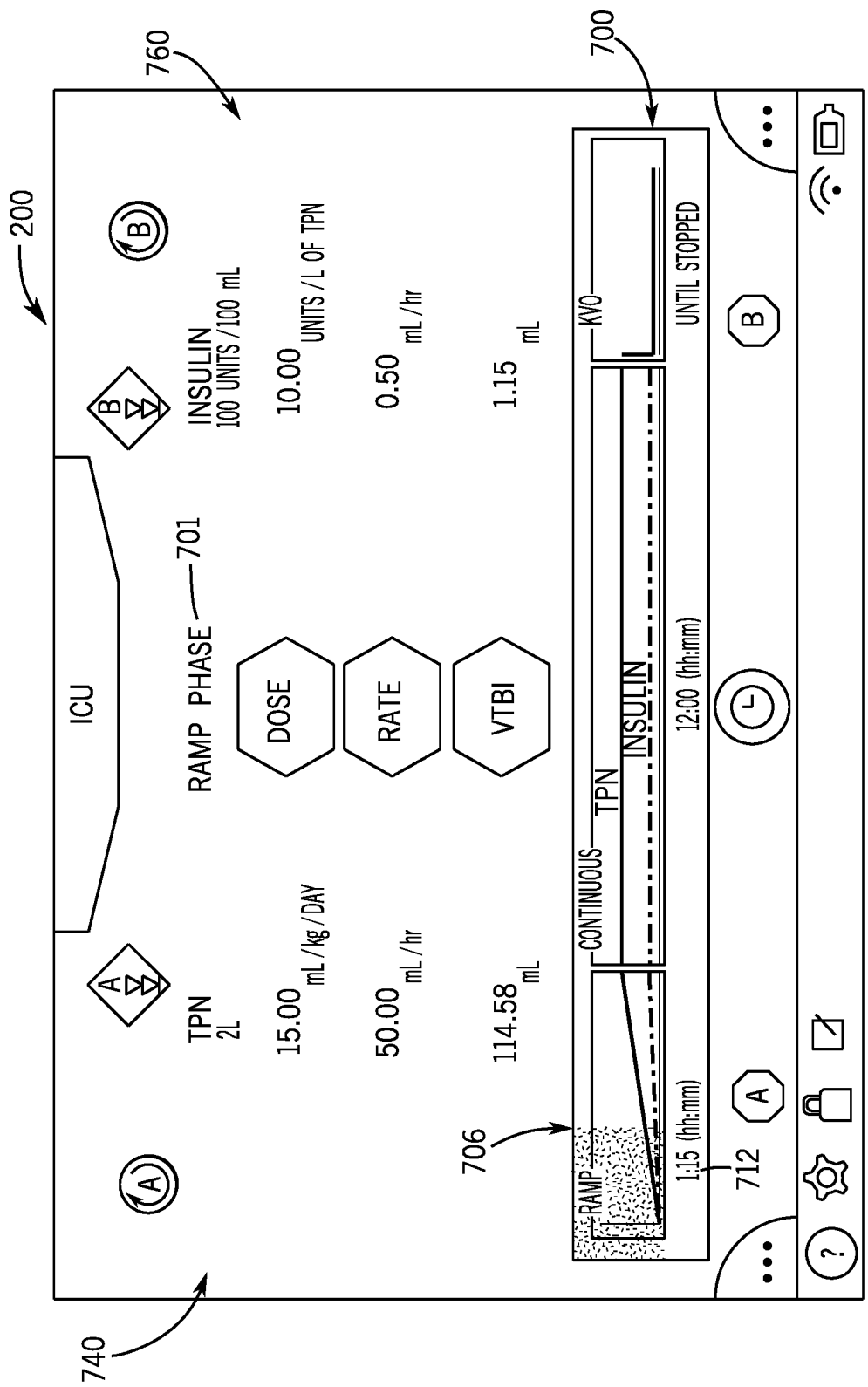

Referring to FIG. 7B, this example shows the user interface 200 with 1:15 (hh:mm) of the ramp phase of the concurrent TPN/insulin infusion remaining, as indicated by the position of the Infusion Progression indicator 706 and the value of the Ramp Phase Time Remaining indicator 712. The Infusion Phase indicator 701 displays the current phase of the concurrent TPN/insulin infusion as the ramp phase. The values presented in the TPN Infusion portion 740 and the Insulin Infusion portion 760 are updated for the present time in the concurrent TPN/insulin infusion.

Figure 7C:
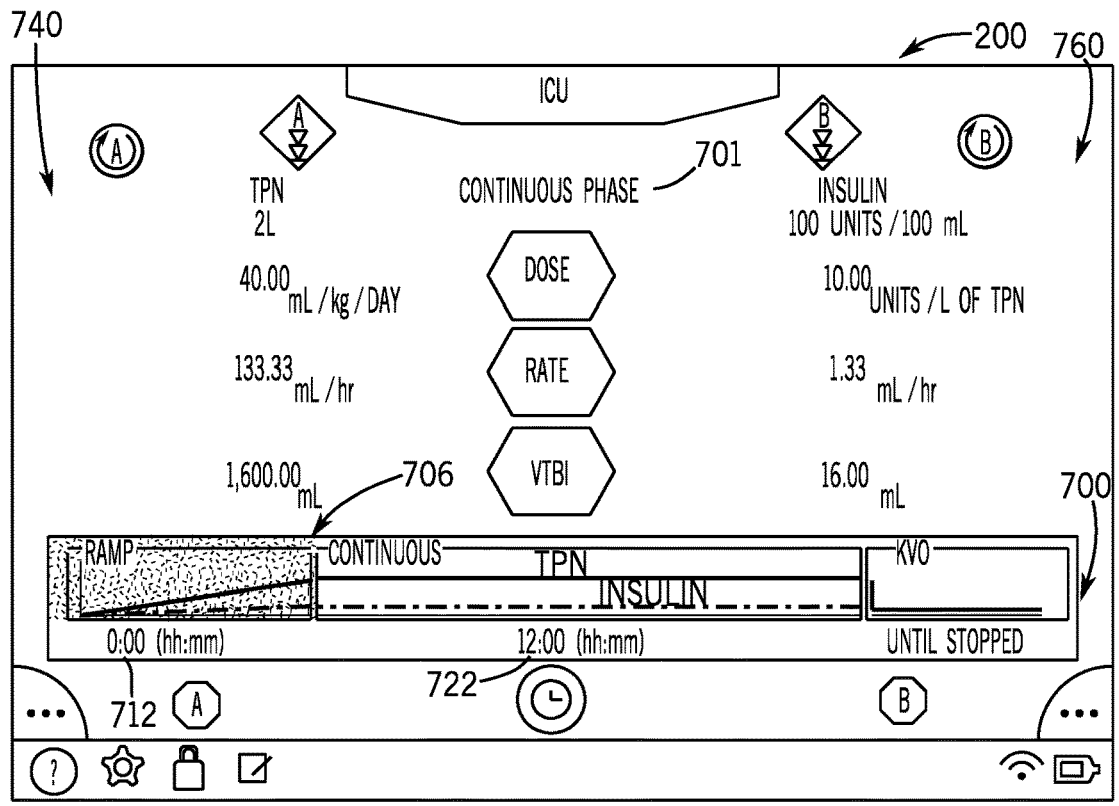

Referring to FIG. 7C, this example shows the user interface 200 at the beginning of the continuous phase of the concurrent TPN/insulin infusion, as indicated by the position of the Infusion Progression indicator 706, the value (0:00) of the Ramp Phase Time Remaining indicator 712, and the value (12:00) of the Continuous Phase Time Remaining indicator 722. The Infusion Phase indicator 701 displays the current phase of the concurrent TPN/insulin infusion as the continuous phase. The values presented in the TPN Infusion portion 740 and the Insulin Infusion portion 760 are updated for the present time in the continuous phase.

Figure 7D:
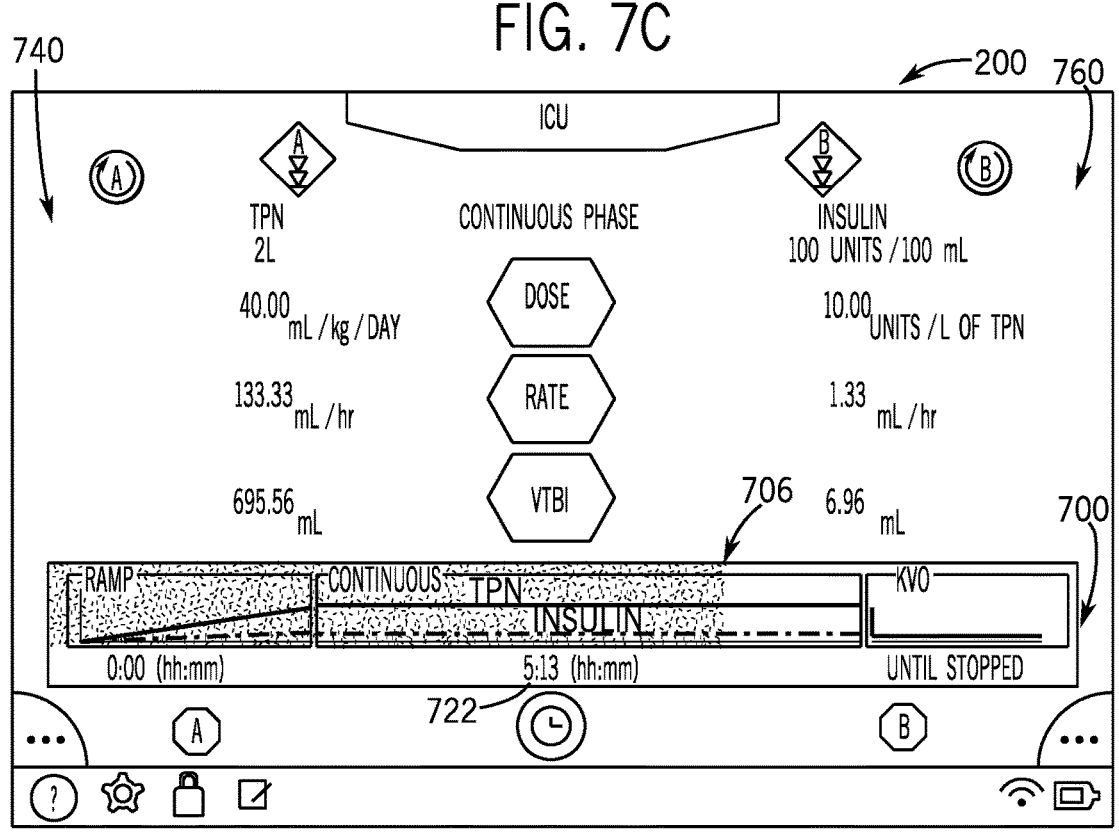

Referring to FIG. 7D, this example shows the user interface 200 during the continuous phase of the concurrent TPN/insulin infusion, as indicated by the position of the Infusion Progression indicator 706 and the value (5:13) of the Continuous Phase Time Remaining indicator 722. The VTBI values presented in the TPN Infusion portion 740 and the Insulin Infusion portion 760 are updated for the present time in the continuous phase. The dose values and rate values remain constant during the continuous phase.

Figure 7E:
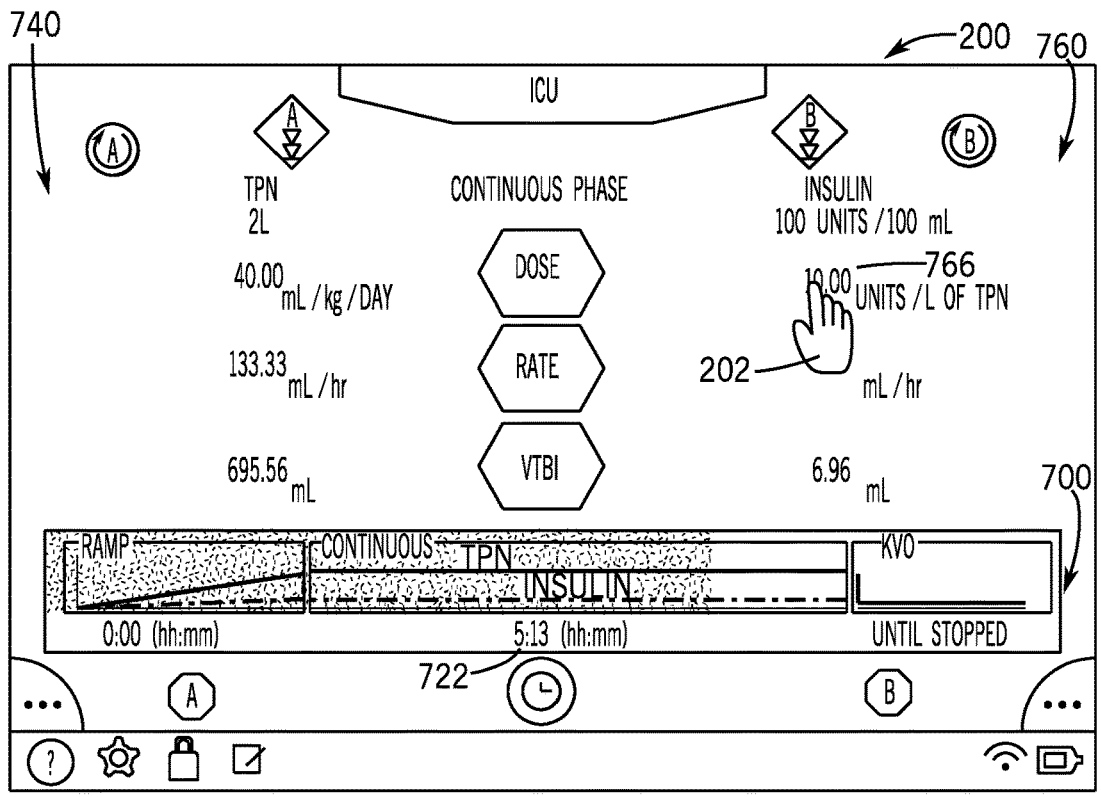
Figure 7F:
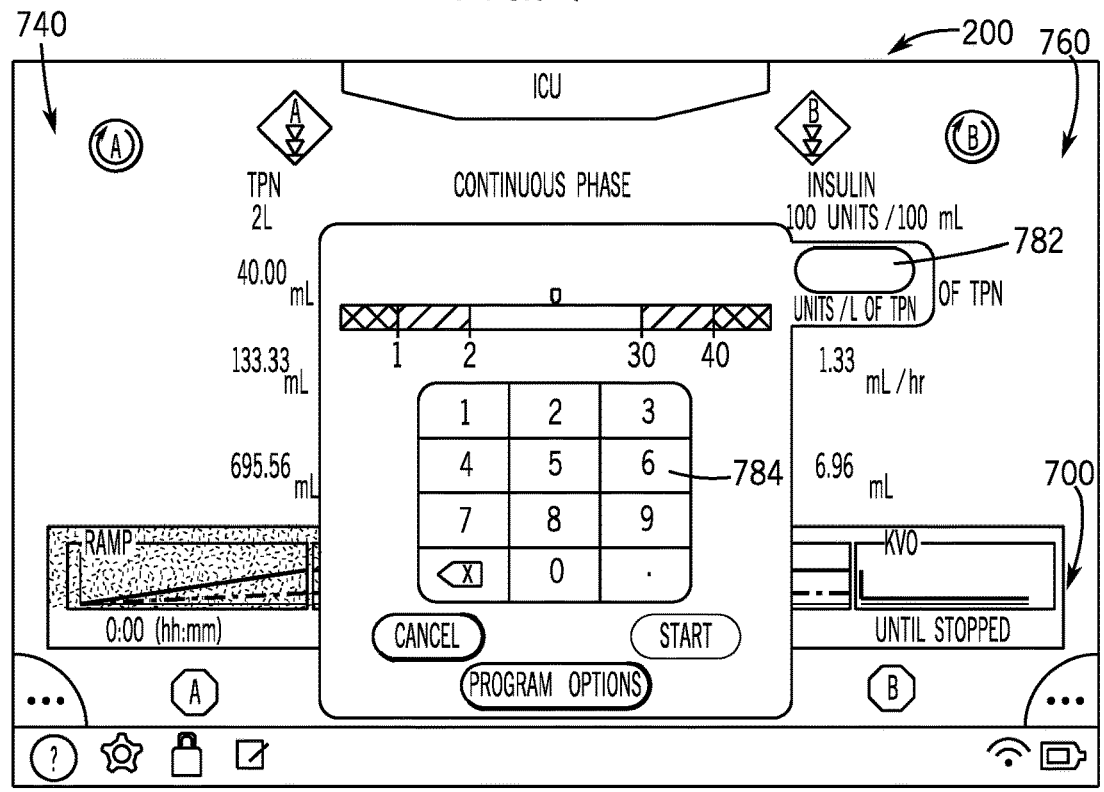
Figure 7G:
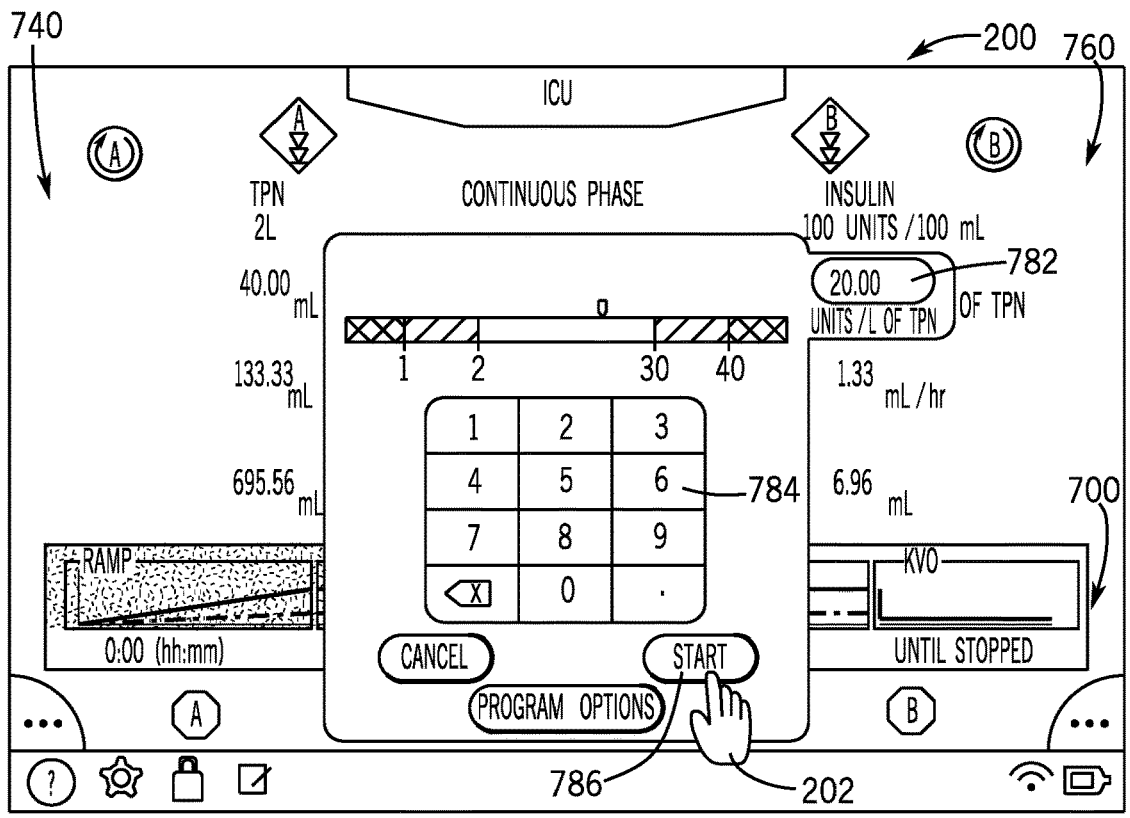
Figure 7H:
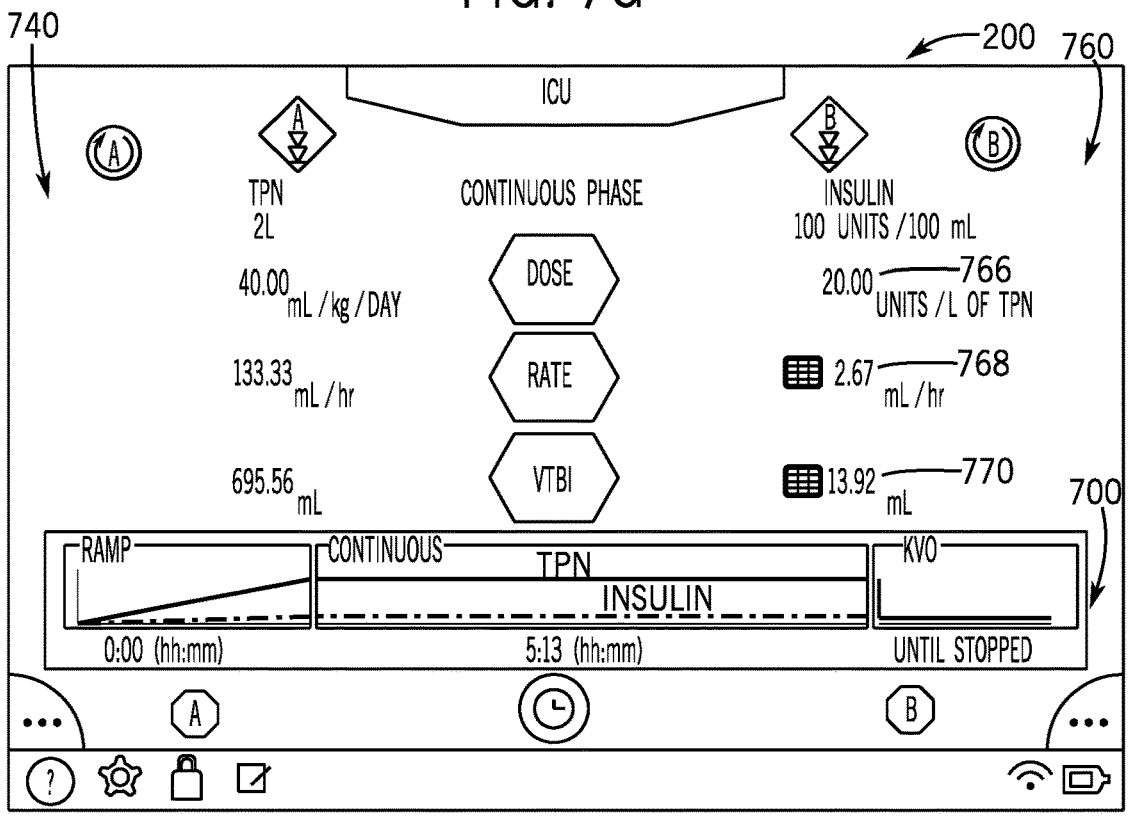

FIGS. 7E-7H illustrate action by the user to titrate the insulin dose, through on the fly changes or hot titration. For example, when the measured blood glucose levels of the patient are elevated above the optimum range, the user 202 can increase the relative insulin infusion (units/L of TPN). Referring to FIG. 7E, the user 202 selects the Insulin Dose indicator 766. Referring to FIG. 7F, the user interface 200 displays a Desired Insulin Dose box 782 and entry keypad 784. Referring to FIG. 7G, the user 202 has entered the new desired insulin dose on the entry keypad 784 and the value of the new desired insulin dose (20 units/L of TPN in place of the previous 10 units/L of TPN) appears in the Desired Insulin Dose box 782. The user 202 selects a Start key 786 to restart the concurrent TPN/insulin infusion. Referring to FIG. 7H, the Insulin Dose indicator 766 displays the value for the new desired insulin dose (20 units/L of TPN), and the Insulin Rate indicator 768 and the Insulin VTBI indicator 770 display values of the insulin rate and the insulin VTBI, respectively, automatically calculated for the new desired insulin dose.

Figure 7I:
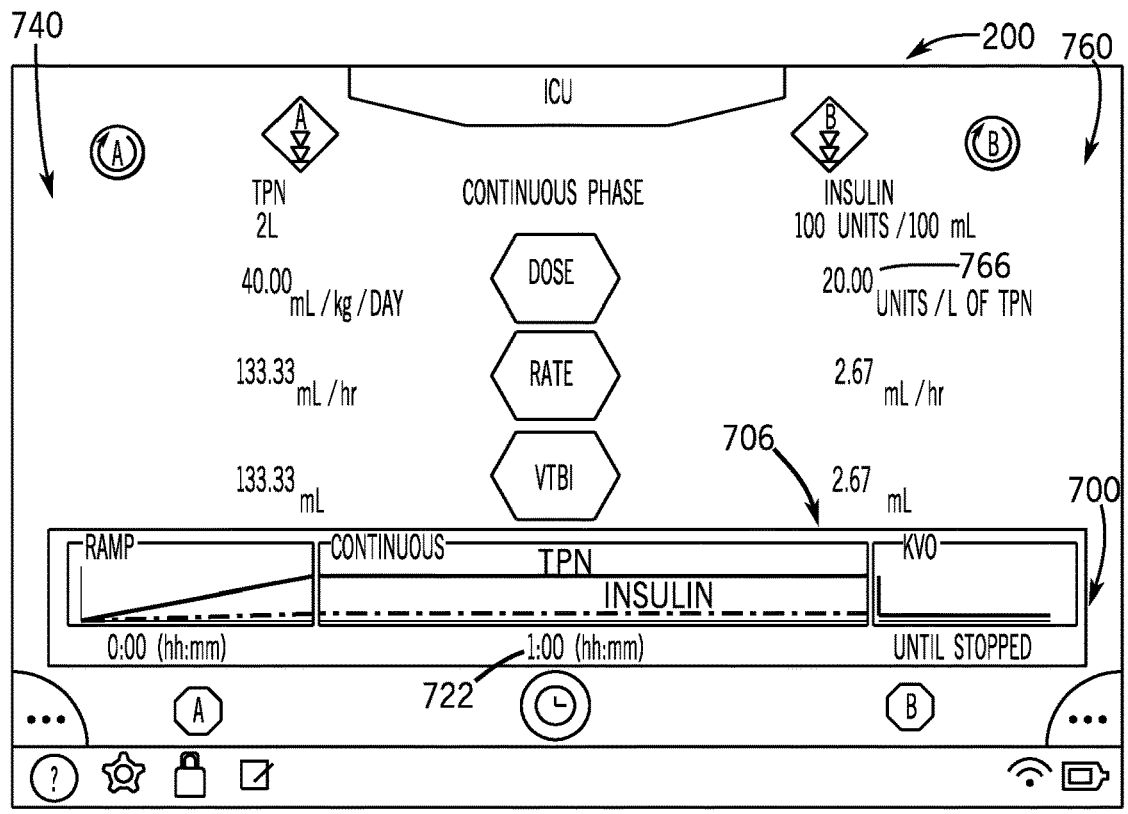

Referring to FIG. 7I, this example shows the user interface 200 during the continuous phase of the concurrent TPN/insulin infusion, as indicated by the position of the Infusion Progression indicator 706 and the value (1:00) of the Continuous Phase Time Remaining indicator 722. The VTBI values presented in the TPN Infusion portion 740 and the Insulin Infusion portion 760 are updated for the present time in the continuous phase. The Insulin Dose indicator 766 continues to display the value for the new desired insulin dose (20 units/L of TPN). The dose values and rate values remain constant during the continuous phase.

Figure 7J:
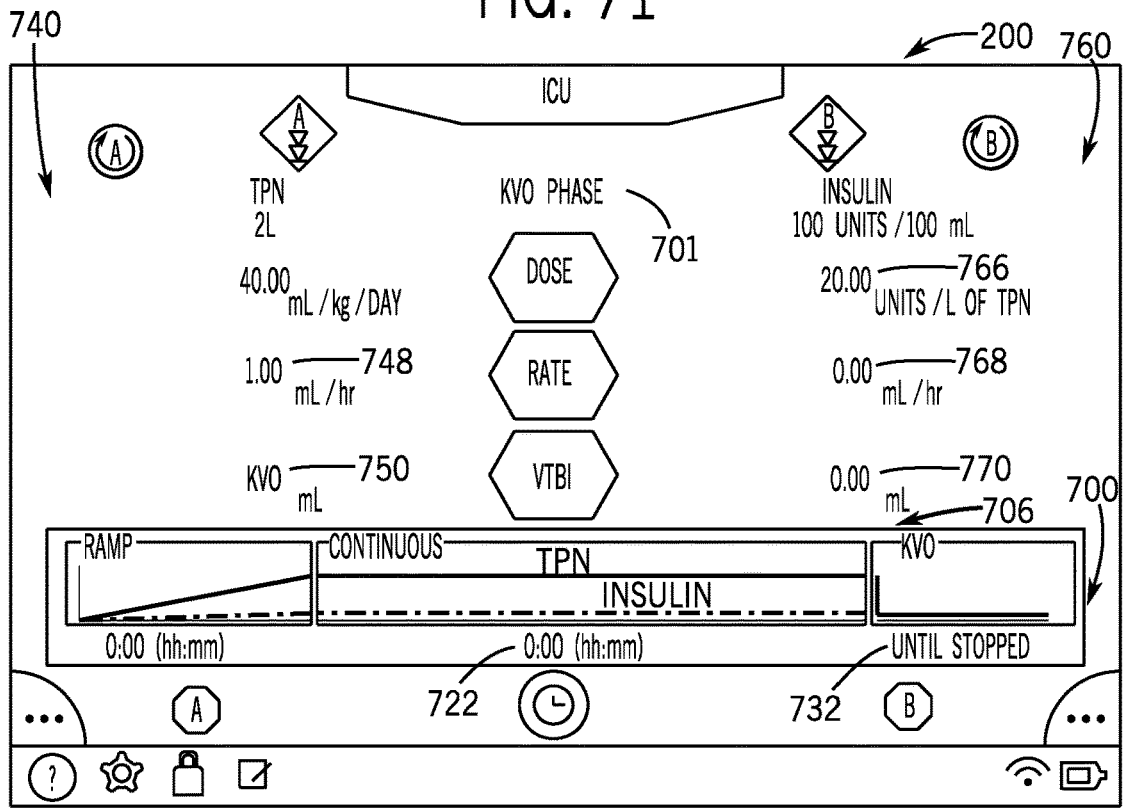

Referring to FIG. 7J, this example shows the user interface 200 at the beginning of the KVO phase of the concurrent TPN/insulin infusion, as indicated by the position of the Infusion Progression indicator 706, the value (0:00) of the Continuous Phase Time Remaining indicator 722, and the value (until stopped) of the KVO Phase Time Remaining indicator 732. The Infusion Phase indicator 701 displays the current phase of the concurrent TPN/insulin infusion as the KVO phase. The values presented in the TPN Infusion portion 740 reflect the End of Infusion Action selected, i.e., the Keep Vein Open (KVO) option with a rate value of one mL/hr displayed in the TPN Dose Rate indicator 748. The TPN VTBI indicator 750 displays KVO to indicate that the KVO phase will continue until stopped. The values presented in the Insulin Infusion portion 760 include the new desired insulin dose (20 units/L of TPN) from the previous continuous phase in the Insulin Dose indicator 766, and values of zero for the Insulin Rate indicator 768 and the Insulin VTBI indicator 770 to indicate that no insulin infusion is being performed during the KVO phase.

Those skilled in the art will appreciate that the concurrent TPN/insulin infusion can include different phases as desired for a particular application. The concurrent TPN/insulin infusion can include TPN ramp, TPN continuous, TPN taper, and/or KVO phases, and combinations thereof. The example of FIG. 7J concludes with a KVO phase. In another example, the concurrent TPN/insulin infusion can conclude with a TPN taper. Those skilled in the art will appreciate that the various phases can be of different durations, which can be input or are selectable by the user 202 via the user interface 200.

Figure 8:
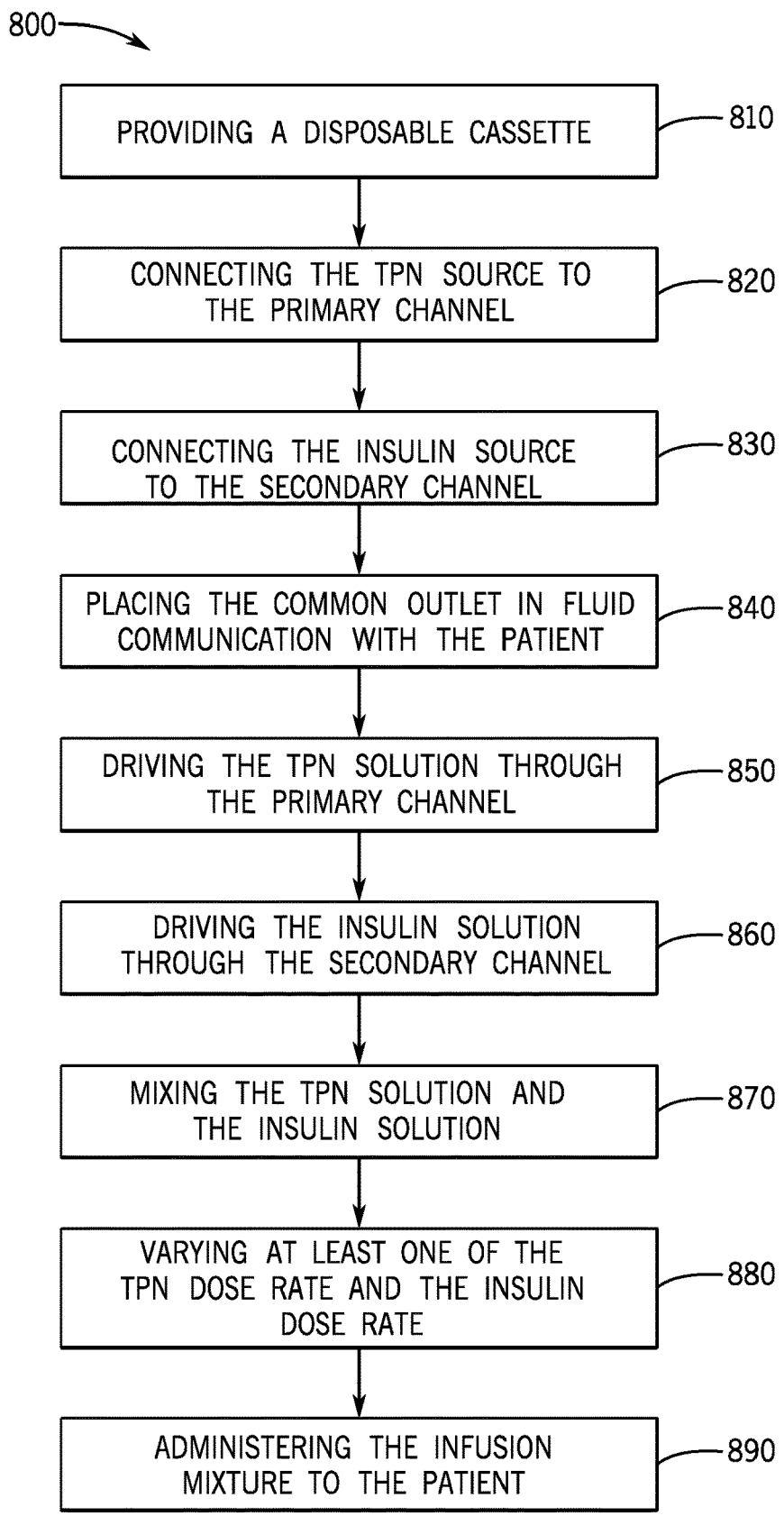
FIG. 8 is a flowchart of a method for concurrently administering a TPN solution and an insulin solution in accordance with the present invention.

FIG. 8 is a flowchart of a method for concurrently administering a TPN solution and an insulin solution in accordance with the present invention. In one embodiment, the method 800 can be performed using the infusion system 100 illustrated in FIG. 1.

Referring to FIG. 8, the method 800 can concurrently administer to a patient a TPN solution from a TPN source and an insulin solution from an insulin source. The method 800 includes: providing a disposable cassette 810 having a primary line, a secondary line, and a common outlet, the primary line and the secondary line being in fluid communication with the common outlet; connecting the TPN source to the primary line 820; connecting the insulin source to the secondary line 830; placing the common outlet in fluid communication with the patient 840; driving the TPN solution through the primary line 850 at a TPN dose rate; driving the insulin solution through the secondary line 860 at an insulin dose rate; mixing the TPN solution and the insulin solution in the disposable cassette to generate an infusion mixture before the common outlet 870; varying at least one of the TPN dose rate and the insulin dose rate 880 to vary a ratio of TPN solution to insulin solution in the infusion mixture; and administering the infusion mixture to the patient 890.

The varying at least one of the TPN dose rate and the insulin dose rate 880 can provide a TPN ramp phase, a TPN continuous phase, a TPN taper phase, and/or a TPN Keep Vein Open (KVO) phase during the concurrent TPN/insulin infusion as desired for a particular application.

To generate the TPN ramp phase, such as can be used at the beginning of the concurrent TPN/insulin infusion, the method 800 can include ramping the TPN dose rate from zero to a continuous phase TPN dose rate. An exemplary TPN ramp phase is illustrated at Ramp portion 610 of FIG. 6. In one embodiment, the method 800 can maintain the insulin dose rate at zero during the TPN ramp phase. In another embodiment, the method 800 can maintain the insulin dose rate at a selected fraction of the TPN solution flow rate during the TPN ramp phase. In yet another embodiment, the method 800 can maintain the insulin dose rate at a continuous phase insulin dose rate during the TPN ramp phase.

To generate the TPN continuous phase, which maintains the TPN dose rate constant, the method 800 can include maintaining the TPN dose rate at a continuous phase TPN dose rate and maintaining the insulin dose rate at a selected fraction of the continuous phase TPN dose rate. An exemplary TPN continuous phase is illustrated at Continuous portion 620 of FIG. 6. Those skilled in the art will appreciate that the insulin dose rate can be adjusted during the TPN continuous phase as desired to manually or automatically adjust for measured glucose levels of the patient.

To generate the TPN taper phase, such as can be used at the end of the concurrent TPN/insulin infusion, the method 800 can include tapering the TPN dose rate from a continuous phase TPN dose rate to a TPN dose rate of zero. An exemplary TPN taper phase is illustrated at TPN Taper option 306 of FIG. 3A. In one embodiment, the method 800 can include maintaining the insulin solution dose rate at zero during the TPN taper phase. In another embodiment, the method 800 can include maintaining the insulin solution dose rate at a selected fraction of the TPN solution dose rate to maintain the ratio of the TPN solution to the insulin solution as constant during the TPN taper phase. In yet another embodiment, the method 800 can include maintaining the insulin solution dose rate at a continuous phase insulin and dose rate during the TPN taper phase.

To generate the TPN Keep Vein Open (KVO) phase, such as can be used at the end of the concurrent TPN/insulin infusion, the method 800 can include decreasing the TPN dose rate from a continuous phase TPN dose rate to a Keep Vein Open (KVO) TPN dose rate. An exemplary TPN KVO phase is illustrated at KVO portion 630 of FIG. 6. Those skilled in the art will appreciate that the various phases can be of different durations, which can be input or are selectable by the user 202 via the user interface 200.

The method 800 can include the user adjusting the insulin flow rate on the fly, i.e., as the concurrent TPN/insulin infusion proceeds, as illustrated in FIGS. 7E-7H. When the insulin dose rate of the driving the insulin solution through the secondary line 860 at an insulin dose rate is a first insulin dose rate, the method 800 can include driving the insulin solution at a second insulin dose rate in response to input of the second insulin dose rate by a user. The second insulin dose rate can adjust for measured glucose levels of the patient.

To avoid hyperglycemia or hypoglycemia in the patient, the method 800 can include monitoring glucose level in the patient and adjusting the insulin dose rate in response to the monitored glucose level. In one embodiment, the method 800 can include changing the insulin dose rate from a first insulin dose rate to a second insulin dose rate in response to the monitored glucose level. In one embodiment, a glucose sensor can provide the monitored glucose level to an insulin therapy calculation system or algorithm, which then automatically programs (auto-programs or auto-populates) the flow controller and populates the user interface with updated delivery parameters, such as rate, volume and duration, and the like.

To allow the user to monitor progress of the concurrent TPN/insulin infusion, the method 800 can include displaying planned values of the TPN dose rate and the insulin dose rate as a function of time on a TPN/Insulin Infusion Plot, and optionally displaying an Infusion Progression indicator at a present infusion time on the TPN/Insulin Infusion Plot. An exemplary TPN/Insulin Infusion Plot is illustrated at TPN/Insulin Infusion Plot portion 700 of FIG. 7A. The TPN/Insulin Infusion Plot portion can include a TPN Infusion profile and an Insulin Infusion profile. In one embodiment, the method 800 can include displaying an infusion portion selected from the group consisting of a Ramp portion, a Continuous portion, a Taper portion, and a KVO portion.

Figure 9:
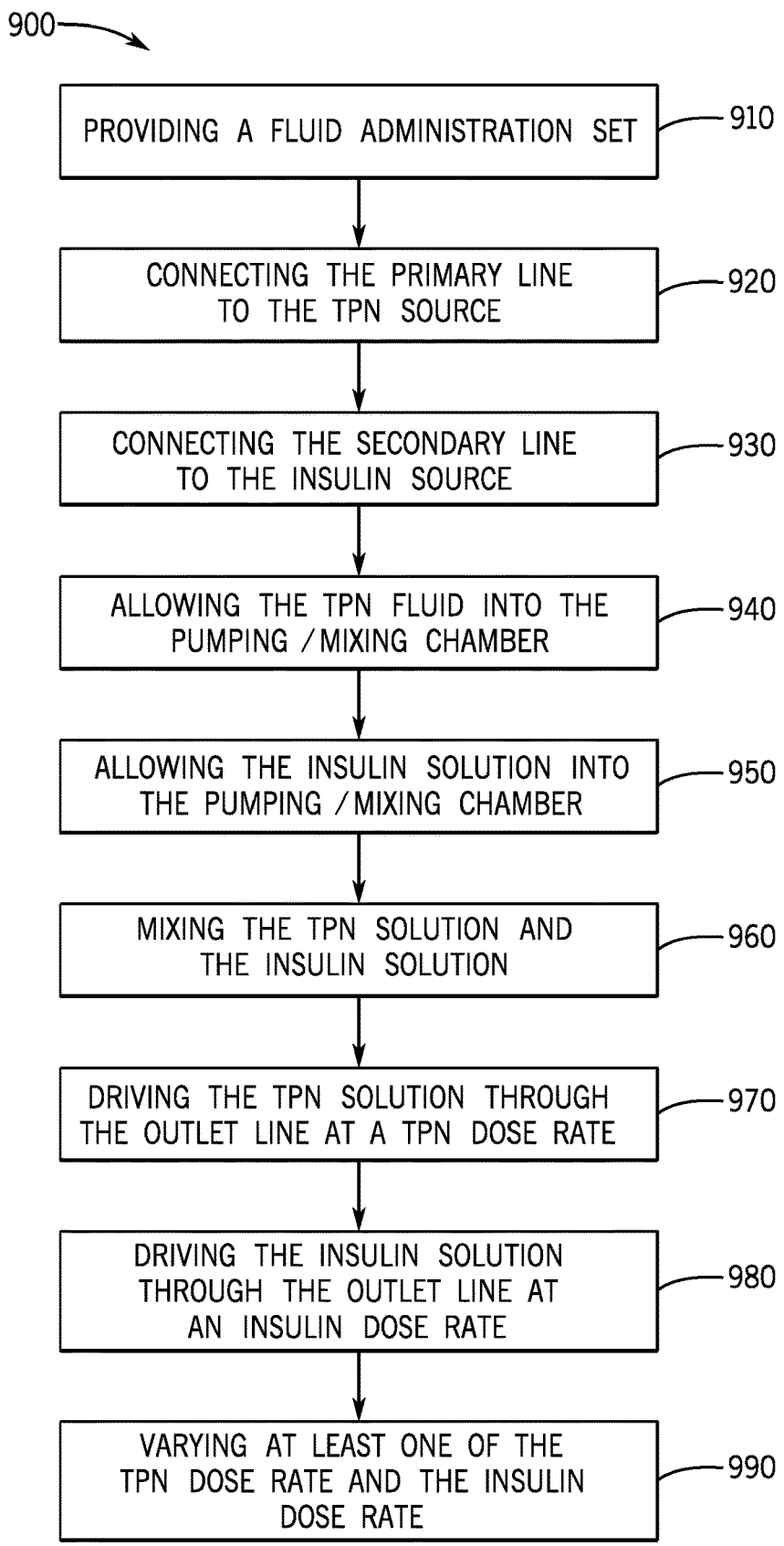
FIG. 9 is a flowchart of another method for concurrently delivering a TPN solution and an insulin solution in accordance with the present invention.

Another embodiment of the invention is shown in FIG. 9. In this embodiment, a method 900 is shown to concurrently deliver a TPN solution from a TPN source container and an insulin solution from an insulin source container that is separate from the TPN source container. The method 900 includes, in step 910, providing a fluid administration set having a primary line, a secondary line, a common outlet line, and a pumping/mixing chamber located between and in fluid communication with the primary line, the secondary line and the common outlet line. The method 900 includes, in step 920, connecting the primary line to the TPN source container and, in step 930, connecting the secondary line to the insulin source container. The method 900 further includes, in step 940, selectively allowing the primary line to feed TPN solution from the primary line to the pumping/mixing chamber and, in step 950, selectively allowing the secondary line to feed insulin solution to the pumping/mixing chamber. The method 900 includes, in step 960, mixing the TPN solution and the insulin solution in the pumping/mixing chamber to generate an infusion mixture before the common outlet line. The method 900 further includes, in step 970, driving with a positive displacement pumping mechanism the TPN solution from the pumping/mixing chamber through the common outlet line at a TPN dose rate, and concurrently with said driving the TPN solution step, in step 980, driving with the positive displacement pumping mechanism the insulin solution from the mixing chamber through the common outlet line at an insulin dose rate. The method 900 also includes, in step 990, varying at least one of the TPN dose rate and the insulin dose rate to vary a ratio of TPN solution to insulin solution in the infusion mixture.

While the embodiments of the invention disclosed herein are presently considered to be preferred, various changes, rearrangement of steps, and modifications can be made without departing from the scope of the invention. The scope of the invention is indicated in the appended claims, and all changes that come within the meaning and range of equivalents are intended to be embraced therein.

The invention claimed is:

1. An infusion system for use with a total parenteral nutrition ("TPN") source of TPN solution and an insulin source of insulin solution to provide concurrent TPN/insulin infusion, the infusion system comprising:
   a fluid administration set having a primary line in fluid communication with the TPN source, a secondary line in fluid communication with the insulin source, and a common outlet line connected to and in operative fluid communication with the primary line and the secondary line;
   a positive displacement pump operable to removably receive the fluid administration set, the pump having a drive mechanism being operable on the fluid administration set to concurrently move the TPN solution through the primary line to the outlet line in response to a TPN solution flow rate signal and the insulin solution through the secondary line to the outlet line in response to an insulin solution flow rate signal;
   a flow controller configured to provide the TPN solution flow rate signal and the insulin solution flow rate signal to the drive mechanism of the pump, wherein the flow controller is further configured to vary the TPN solution flow rate signal and the insulin solution flow rate signal to vary a ratio of TPN solution to insulin solution provided to the common outlet;
   a glucose sensor operably connected to the patient to monitor glucose level and further operable connected to the flow controller; and
   wherein the flow controller comprises instructions that when executed are configured to:
      display a first user interface including a plurality of user selectable modes for concurrent TPN/insulin infusion, wherein the plurality of user selectable modes comprise continuous phase, taper phase, and keep vein open phase,
      display a second user interface that is customized based on a first user selection of one of the user selectable modes in the first user interface;
      display a third user interface that includes insulin infusion options, said insulin infusion options configured to enable independent titration of insulin delivery or link the insulin delivery to TPN delivery; and
      display a fourth user interface that illustrates TPN infusion profile and insulin infusion profile on a same timeline, said fourth user interface including a start key configured to initiate the concurrent TPN/insulin infusion;
      wherein the flow controller is further configured to automatically control the insulin solution flow rate signal while the TPN solution is being delivered based on the monitored glucose level.

2. The infusion system of claim 1 wherein the flow controller is further operable to ramp the TPN solution flow rate signal from a value corresponding to a TPN dose rate of zero to a value corresponding to a continuous phase TPN dose rate over a user selectable duration in a TPN ramp phase.

3. The infusion system of claim 2 wherein the flow controller is further operable to maintain the insulin solution flow rate signal at a value corresponding to an insulin dose rate of zero during the TPN ramp phase.

4. The infusion system of claim 2 wherein the flow controller is further operable to maintain the insulin solution flow rate signal as a selected fraction of the TPN solution flow rate signal during the TPN ramp phase.

5. The infusion system of claim 2 wherein the flow controller is further operable to maintain the insulin solution flow rate signal at a value corresponding to a continuous phase insulin dose rate during the TPN ramp phase.

6. The infusion system of claim 1 wherein the flow controller is further operable to maintain the TPN solution flow rate signal at a value corresponding to a continuous phase TPN dose rate and to maintain the insulin solution flow rate signal at a selected fraction of the TPN solution flow rate signal during the TPN continuous phase.

7. The infusion system of claim 1 wherein the flow controller is further operable to taper the TPN solution flow rate signal over a user selectable duration from a value corresponding to a continuous phase TPN dose rate to a value corresponding to a TPN dose rate of zero during TPN taper phase.

8. The infusion system of claim 7 wherein the flow controller is further operable to maintain the insulin solution flow rate signal at a value corresponding to an insulin dose rate of zero during the TPN taper phase.

9. The infusion system of claim 7 wherein the flow controller is further operable to maintain the insulin solution flow rate signal as a selected fraction of the TPN solution flow rate signal to maintain the ratio of the TPN solution to the insulin solution constant during the TPN taper phase.

10. The infusion system of claim 7 wherein the flow controller is further operable to maintain the insulin solution flow rate signal at a value corresponding to a continuous phase insulin dose rate during the TPN taper phase.

11. The infusion system of claim 1 wherein the flow controller is further operable to decrease the TPN solution flow rate signal over a user selectable duration from a value corresponding to a continuous phase TPN dose rate to a value corresponding to a Keep Vein Open (KVO) TPN dose rate after a TPN continuous phase.

12. The infusion system of claim 1 wherein the flow controller is further operable to vary the insulin solution flow rate signal from a first insulin solution flow rate signal to a second insulin solution flow rate signal in response to input of the second insulin solution flow rate signal by a user.

13. The infusion system of claim 1 wherein the flow controller is further operable to vary the insulin solution flow rate signal from a first insulin solution flow rate signal to a second insulin solution flow rate signal in response to the glucose signal.

14. The infusion system of claim 1 wherein the user interface is further operable to display an Infusion Progression indicator on the TPN/Insulin Infusion Plot portion, the Infusion Progression indicator being operable to indicate a current state of the concurrent TPN/insulin infusion.

15. The infusion system of claim 1 wherein the user interface is further operable to display an infusion portion selected from the group consisting of a Ramp portion, a Continuous portion, a Taper portion, and a KVO portion.

16. The infusion system of claim 1 wherein the administration set comprises a cassette including a primary inlet joining a primary fluid passageway into fluid communication with the primary line, a secondary inlet joining a secondary fluid passageway into fluid communication with the secondary line, an outlet in fluid communication with the outlet line, and a pumping/mixing chamber covered by a resilient flexible membrane and in fluid communication with the primary fluid passageway, the secondary fluid passageway and the outlet.

17. The infusion system of claim 16 wherein the drive mechanism comprises a motor driving a plunger into the membrane covering the pumping/mixing chamber while operating a primary inlet valve, a secondary inlet valve and an outlet valve so as to mix and displace fluid from the pumping/mixing chamber through the outlet into the outlet line.

* * * * *